United States Patent
Elbert et al.

(10) Patent No.: US 10,137,082 B2
(45) Date of Patent: Nov. 27, 2018

(54) HYDROGEL MICROPARTICLE SCAFFOLD WITH GRADIENTS OF DEGRADABILITY AND METHODS THEREOF

(71) Applicants: Donald L. Elbert, St. Louis, MO (US); Jacob Roam, St. Louis, MO (US)

(72) Inventors: Donald L. Elbert, St. Louis, MO (US); Jacob Roam, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 15/683,470

(22) Filed: Aug. 22, 2017

(65) Prior Publication Data

US 2018/0049977 A1 Feb. 22, 2018

Related U.S. Application Data

(60) Provisional application No. 62/378,013, filed on Aug. 22, 2016.

(51) Int. Cl.
| | |
|---|---|
| *A61K 9/00* | (2006.01) |
| *A61K 47/36* | (2006.01) |
| *A61K 47/69* | (2017.01) |
| *C08B 37/00* | (2006.01) |
| C07K 14/78 | (2006.01) |
| C07K 14/475 | (2006.01) |

(52) U.S. Cl.
CPC .......... *A61K 9/0024* (2013.01); *A61K 47/36* (2013.01); *A61K 47/6903* (2017.08); *C08B 37/0075* (2013.01); *C07K 14/4756* (2013.01); *C07K 14/78* (2013.01)

(58) Field of Classification Search
CPC ...................................................... C01K 7/06
See application file for complete search history.

(56) References Cited

U.S. PATENT DOCUMENTS

| | | |
|---|---|---|
| 8,557,288 B2 | 10/2013 | Elbert et al. |
| 8,790,678 B2 | 7/2014 | Elbert et al. |

OTHER PUBLICATIONS

Luo, Y. et al., "A photolabile hydrogel for guided three-dimensional cell growth and migration," Nat. Mater., 2004, pp. 249-253, vol. 3.

Ravindran, S. et al., "Changes of chondrocyte expression profiles in human MSC aggregates in the presence of PEG microspheres and TGF-beta3," NIH Public Access Author Manuscript, available in PMC Nov. 1, 2012, pp. 1-20, published in final edited form as: Biomaterials., Nov. 2011, p. 8436-8445, vol. 32, No. 33.

Roam, J. et al., "A modular, plasmin-sensitive, clickable poly(ethylene glycol)-heparin-laminin microsphere system for establishing growth factor gradients in nerve guidance conduits," Biomaterials., Dec. 2015, pp. 112-124, vol. 72, with HHS Public Access, Author Manuscript, Dec. 1, 2016, pp. 1-29.

Roam, J. et al., "Controlled Release and Gradient Formation of Human Glial-Cell Derived Neurotrophic Factor from Heparinated Poly(ethylene glycol) Microsphere-based Scaffolds," NIH Public Access Author Manuscript, available in PMC on Aug. 1, 2015, pp. 1-23, published in final edited form as: Biomaterials., Aug. 2014, pp. 6473-6481, vol. 35, No. 24.

Roam, J. et al., "The Formation of Protein Concentration Gradients Mediated by Density Differences of Poly(ethylene glycol) Microspheres," NIH Public Access Author Manuscript, available in PMC on Nov. 1, 2011, pp. 1-22, published in final edited form as: Biomaterials., Nov. 2010, pp. 8642-8650, vol. 31, No. 33.

Scott, E. et al., "Modular scaffolds assembled around living cells using poly(ethylene glycol) microspheres with macroporation via a non-cytotoxic porogen," NIH Public Access Author Manuscript, available in PMC on Jan. 1, 2011, pp. 1-19, published in final edited form as: Acta Biomater., Jan. 2010, pp. 29-38, vol. 6, No. 1.

Scott, R. et al., "Modular Poly(Ethylene Glycol) Scaffolds Provide the Ability to Decouple the Effects of Stiffness and Protein Concentration on PC12 Cells," NIH Public Access Author Manuscript, available in PMC on Nov. 1, 2012, pp. 1-20, published in final edited form as: Acta Biomater., Nov. 2011, pp. 3841-3849, vol. 7, No. 11.

Smith, A. et al., "Long-term culture of HL-1 cardiomyocytes in modular poly(ethylene glycol) microsphere-based scaffolds crosslinked in the phase-separated state," NIH Public Access Author Manuscript, available in PMC on Jan. 1, 2013, pp. 1-22, published in final edited form as: Acta Biomater., Jan. 2012, pp. 31-40, vol. 8, No. 1.

*Primary Examiner* — Kyle A Purdy
(74) *Attorney, Agent, or Firm* — Polsinelli PC

(57) ABSTRACT

Disclosed herein is a device and method for regenerating tissue using a modular scaffold having a gradient of enzymatic degradability. The disclosure further relates to scaffolds made of microparticles comprising a cross-linked water-soluble polymer or cross-linked water-soluble polymers and a process for forming thereof.

18 Claims, 30 Drawing Sheets
(23 of 30 Drawing Sheet(s) Filed in Color)

PEG-(VRN)₈          PEG₈-VS

Clickable PEG

HYDROGEL MICROPARTICLE SCAFFOLD WITH GRADIENTS OF DEGRADABILITY AND METHODS THEREOF

CROSS REFERENCE TO RELATED APPLICATIONS

This application claims the benefit of U.S. Provisional Application No. 62/378,013, filed Aug. 22, 2016, which is hereby incorporated by reference in its entirety.

GOVERNMENT SUPPORT

This invention was made with government support under R21 NS077765 awarded by the National Institutes of Health. The government has certain rights in the invention.

FIELD

The present invention relates to the generation of pathways for cell migration via self-assembly of particles caused by differences in physical properties of intraparticle crosslinks versus interparticle crosslinks.

BACKGROUND OF INVENTION

Macroporous hydrogels for tissue engineering scaffolds are ideally formed from a water-soluble polymer such as poly(ethylene glycol) (PEG). One problem with pure PEG hydrogels as scaffolds, however, is that it can be difficult for cells to infiltrate and degrade them due to their density and homogeneity at the cell scale. Macroporous hydrogels, therefore, are desirable but require incorporation of a pore-forming substance (porogen), which may be difficult to control (e.g., a foaming agent) or remove (e.g., poly(methylmethacrylate) microbeads). Porous hydrogels may become mechanically weak if porosity reaches a high degree, but a high degree of porosity is desirable for cell migration into the scaffold so that pores are highly connected. Materials that are strong enough to be highly porous typically have poor biocompatibility compared to hydrogels. Cell migration into the scaffold is desirable in the generation of new functional tissues induced by implanted biomaterials.

In one example, peripheral nerve regeneration is a complex problem that, despite many advancements and innovations, still has sub-optimal outcomes. Compared to biologically derived acellular nerve grafts and autografts, completely synthetic nerve guidance conduits (NGC), which allow for precise engineering of their properties, are promising but still far from optimal. If the conduit contains a homogenous degradable material, cells may dissolve the material uniformly but too slowly or too quickly to allow rapid cell migration.

Therefore, there is a need for creating multifunctional macroporous hydrogel scaffolds with microscale gradients in cell-initiated degradability to provide pathways for cell migration.

SUMMARY OF INVENTION

Provided herein, in an aspect, is modular scaffold comprising a plurality of hydrogel microparticles. The hydrogel microparticles are crosslinked together with at least some crosslinks having tunable rates of enzymatic degradation. The scaffold may include a gradient of degradation between the microparticles, and microparticles with at least two different rates of degradability may be layered to form the gradient of degradation in the scaffold at length scales greater than the mean size of the microparticles. The crosslinks with tunable degradation may include a plasmin sensitive peptide sequence, such as Ac-GCGGVRNGGK—NH2, as one example of the multitude of peptide sequences that are sensitive to plasmin, including sequences not found in natural proteins. In an aspect, the crosslinks between the microparticles may fully degrade before the bulk of the microparticles fully degrades. The microparticles may include a cross-linked water-soluble polymer selected from the group consisting of polyacrylate, polyacrylamide, poly(acrylamide sulphonic acid), polyacrylonitrile, polyamines, poly(ethylene glycol), poly(ethylene imine), poly(ethylene oxide), poly(ethyloxazoline), polyhydroxyethylacrylate, polymethacrylate, polymethacrylamide, poly(oxyalkylene oxide), poly(propylene oxide), polyurethane, poly(vinyl alcohol), poly(vinyl pyrrolidone), and combinations thereof. In an aspect, at least a portion of the crosslinks between the microparticles are formed using Click chemistry. Click chemistry is defined herein as a reaction between two chemical groups, neither of which are capable of rapid reaction with chemical groups found on proteins under physiological conditions. For purposes herein, reaction of vinyl sulfone with a thiol is not considered to be a click reaction. An example of a click reaction is an azide with a strained alkyne in the absence of copper. The microparticles may further include a functional agent selected from the group consisting of cell adhesion proteins, growth factors, extra cellular matrix components, and combinations thereof. The cell adhesion protein may be laminin, and the growth factor may be glial cell-derived neurotrophic factor (GDNF). The microparticles may further include heparin to control the rate of the growth factor release, and the heparin content of the microparticles may be greater than about 3% by weight. The heparin may also interact with endogenous growth factors, and may aid in cell adhesion via cell receptors specific for glycosaminoglycans. The scaffold may include a concentration gradient of the functional agent. In an aspect, the scaffold may be contained within a nerve guidance conduit. In another aspect, the scaffold may be seeded with or encourage the in-growth of cells selected from the group consisting of fibroblasts, epithelial cells, blood cells, precursor blood cells, immune system cells, hepatocytes, renal cells, chondrocytes, osteoblasts, respiratory tract cells, gut cells, bladder cells, pancreatic cells, myoblasts, skeletal muscle cells, heart muscle cells, smooth muscle cells, exocrine gland cells, hormone secreting cells, sensory transducer cells, neurons, neuron supporting cells, stem cells, and combinations thereof.

Further provided herein is a method of forming a modular scaffold comprising hydrogel microparticles. The method may include combining a water-soluble polymer with a plasmin degradable water-soluble polymer at a 1:1 molar ratio; incubating the PEG solution above the LCST for different times between about 8 min and about 45 minutes to form microparticles with distinct plasmin degradability correlated with crosslinking time, and further controlled by the peptide sequence; layering the microparticles with different plasmin degradability to create a scaffold with a gradient of plasmin degradability. In an aspect, the water-soluble polymer may be $PEG_8$-VS. The method may further include adding clickable PEG at a ratio of 50:1 water-soluble polymer to clickable PEG. The method may further include incubating the microparticles with laminin prior to creating the scaffold. In another aspect, the method may further include incubating the microparticles with thiolated heparin prior to creating the scaffold, and the microparticles may be further incubated with GDNF, where the heparin controls the release rate of the GDNF. The method may include quenching thiol and amine reactive chemical groups with a thiol-containing compound prior to addition of GDNF. The method may further include placing the scaffold within a nerve guidance conduit, allowing the microparticles to crosslink together via clickable groups. The method may further include seeding the scaffold with cells selected from the group consisting of fibroblasts, epithelial cells, blood cells, precursor blood cells, immune system cells, hepatocytes, renal cells, chondrocytes, osteoblasts, respiratory tract cells, gut cells, bladder cells, pancreatic cells, myoblasts, skeletal muscle cells, heart muscle cells, smooth muscle cells, exocrine gland cells, hormone secreting cells, sensory transducer cells, neurons, neuron supporting cells, stem cells, and combinations thereof.

Also provided herein is a method for regenerating a tissue. The method may include implanting a modular scaffold comprising a plurality of hydrogel microparticles, where the hydrogel microparticles are crosslinked together with at least some crosslinks having tunable rates of enzymatic degradation. The scaffold may include a gradient of plasmin degradability between the microparticles, and the crosslinks between the microparticles may degrade before the bulk of the microparticles degrade. In an aspect, the tunability is due to differences in crosslink density between microspheres versus the crosslink density within microspheres. The microparticles may include a cross-linked water-soluble polymer. At least a portion of the crosslinks between the microparticles are formed using Click chemistry. The microparticles may further include a functional agent selected from the group consisting of cell adhesion proteins, growth factors, extra cellular matrix components, and combinations thereof. In an aspect, the cell adhesion protein may be laminin and the growth factor may be glial cell-derived neurotrophic factor (GDNF). The microparticles may further comprise heparin to control the rate of the growth factor release. The scaffold may include a concentration gradient of the functional agent. The scaffold may be contained within a nerve guidance conduit. In an aspect, the scaffold may be seeded with or encourage the in-growth of cells selected from the group consisting of fibroblasts, epithelial cells, blood cells, precursor blood cells, immune system cells, hepatocytes, renal cells, chondrocytes, osteoblasts, respiratory tract cells, gut cells, bladder cells, pancreatic cells, myoblasts, skeletal muscle cells, heart muscle cells, smooth muscle cells, exocrine gland cells, hormone secreting cells, sensory transducer cells, neurons, neuron supporting cells, stem cells, and combinations thereof. The tissue to be regenerated may be neural tissue or vascular tissue.

Additional embodiments and features are set forth in part in the description that follows, and will become apparent to those skilled in the art upon examination of the specification or may be learned by the practice of the disclosed subject matter. A further understanding of the nature and advantages of the disclosure may be realized by reference to the remaining portions of the specification and the drawings, which forms a part of this disclosure.

BRIEF DESCRIPTION OF DRAWINGS

The application file contains at least one drawing executed in color. Copies of this patent application publication with color drawing(s) will be provided by the Office upon request and payment of the necessary fee.

The description will be more fully understood with reference to the following figures and data graphs, which are presented as various embodiments of the disclosure and should not be construed as a complete recitation of the scope of the disclosure, wherein:

FIG. 3A shows PEG-(VRN)$_8$ and PEG$_8$-VS (200 mg/mL) were combined at 1:1 molar ratio and incubated at 37° C. for 1 h. FIG. 3B shows PEG$_8$-Azide/Amine and PEG$_8$-Cyclooctyne/Amine were added at 1:50 click PEG to non-click PEG ratio. FIG. 3C shows PEG was diluted to 20 mg/mL in 0.6 M Na$_2$SO$_4$ and incubated 8-10 min at 70° C. FIG. 3D shows microparticles were washed 3× in PBS and thiolated heparin (2.6 mg/mL) and laminin (20 mg/mL) were added to suspended µspheres and incubated at 25° C. overnight. Microparticles were washed 2× in low salt buffer. FIG. 3E shows cysteine (2.5 mg/mL) was added and incubated 25° C. for 30 min to cap remaining vinylsulfones. Microparticles were washed 2× in low salt buffer. FIG. 3F shows the two microparticle types were combined prior to growth factor loading and/or scaffold formation.

(FIG. 16A) At 25° C., a monomodal size distribution results. (FIG. 16B) At 37° C., bimodal size distribution results. In FIG. 16A, a true precipitation polymerization likely leads to the monomodal distribution. In FIG. 16B, both coacervation polymerization and precipitation polymerization likely occur. The initiator is likely soluble in both polymer-rich and solvent-rich domains. In the polymer-rich domain, coacervation polymerization results. In the solvent-rich domain, the small amount of polymer still in solution undergoes a precipitation polymerization.

DETAILED DESCRIPTION

Figure 1A:
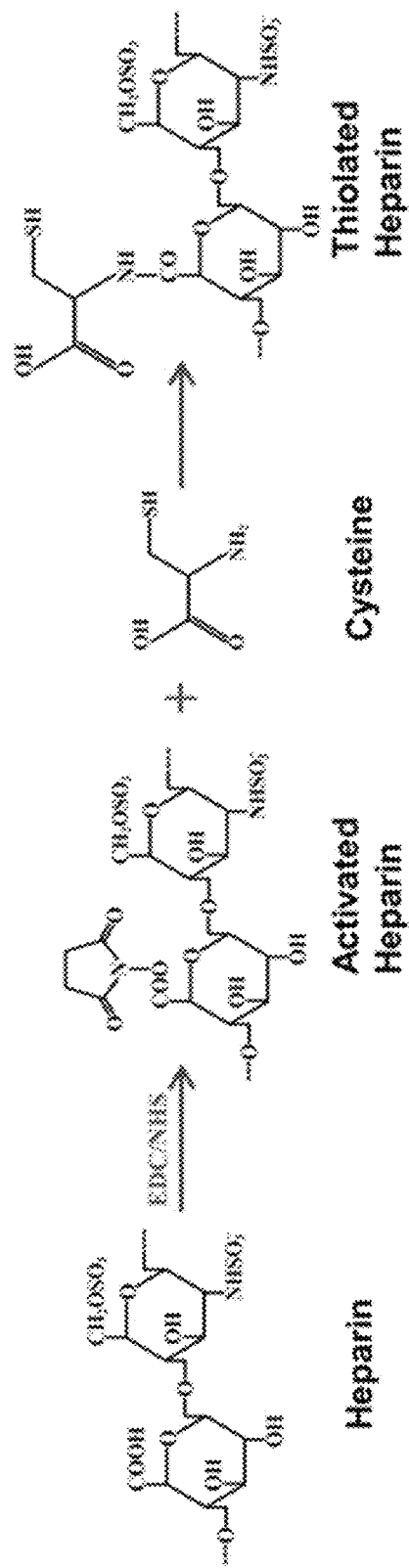
FIG. 1A shows a reaction scheme for the thiolation of heparin.

The disclosure may be understood by reference to the following detailed description, taken in conjunction with the drawings as described below. It is noted that, for purposes of illustrative clarity, certain elements in various drawings may not be drawn to scale.

Provided herein are modular scaffolds for tissue engineering or tissue regeneration. The modular scaffolds include multifunctional hydrogel microparticles, such that microparticles with varying properties may be assembled together in various ways to give the scaffold modular functionality. For example, the scaffold may be formed of layers of crosslinked microparticles, where each layer of microparticles has a different functionality or degree of functionality. In an aspect, the microparticles may have varying degradability between the crosslinked microparticles. Other functional agents that the microparticles may have include cell adhesion proteins, growth factors, or other extra cellular matrix proteins. In an aspect, the scaffold may include a gradient of degradability between the crosslinked microparticles to promote cell migration into and through the scaffold. The gradient of degradability may be a gradient of enzymatic degradability. For example, the gradient of degradability between the microparticles may be cell-initiated, such that the crosslinks between the microparticles degrade faster than the crosslinks within the microparticles. Thus, the migrating cells may create a "path" through the scaffold by releasing plasmin and selectively degrading the crosslinks between the microparticles, while maintaining attachment to the bulk of the microsphere. Without being limited to a particular theory, the gradient of degradability may allow for the more distal portion of the scaffold to remain crosslinked until it is reached by a migrating cell.

I. Microparticles

As used herein in particular embodiments of the present disclosure, the terms "microparticle," "microsphere," "microgel," and "nanogel" are used interchangeably and refer to crosslinked polymer networks that range from about 10 nm in diameter to about 100 microns in diameter, preferably 3-20 microns (a) Polymers As will be appreciated by a skilled artisan, a variety of water-soluble polymers can be used in the present disclosure. In general, the water-soluble polymer is a hydrophilic polymer. Non-limiting examples of exemplary hydrophilic polymers include, but are not limited to, polyacrylate, polyacrylamide, poly(acrylamide sulphonic acid), polyacrylonitrile, polyamines, poly(ethylene glycol), poly(ethylene imine), poly(ethylene oxide), poly(ethyloxazoline), polyhydroxyethylacrylate, polymethacrylate, polymethacrylamide, poly(oxyalkylene oxide), poly(propylene oxide), polyurethane, poly(vinyl alcohol), and poly(vinyl pyrrolidone). Preferentially, polymers with the highest second virial coefficients in water are desirable, such that they exhibit non-linear and increasing osmotic pressures as a function of concentration. Such polymers include, for example, poly(ethylene glycol) (PEG) and poly(vinyl pyrrolidone) (PVP).

At least one of the water-soluble polymers used in the process of the present disclosure will have a LCST greater than 37° C. in water. Examples of hydrophilic polymers that meet this criterion include, for example, hydroxypropylcellulose (LCST=45° C.), poly(ethyloxazoline) (LCST=60-78° C.), poly(ethylene glycol)/poly(ethylene oxide) (LCST=95-150° C.) and poly(vinyl pyrrolidone) (LCST=140-179° C.). In some embodiments, the water-soluble polymer used to make microparticles of cross-linked polymer may be poly(ethylene glycol) or poly(vinyl pyrrolidone).

The monomers and/or macromers of the water-soluble polymers will generally have a functionality of greater than or equal to 2. For example, the monomers/macromers may have a functionality of 3, 4, 5, 6, 7, 8, 9, 10, and so forth. Functionality may be due to the presence of an unsaturated bond or the presence of a functional end-group. Exemplary functional end-groups include sulfones, maleimides, sulfoxides, sulfonates, sulfonamides, sulfhydryls, phosphonates, phosphonamides, acrylates, amines, alkynes, azides, isocyanates, halides, hydroxyls, carboxyls, and esters. Exemplary functional groups include vinylsulfone, amine, and acrylate.

The monomers and/or macromers of the water-soluble polymer will generally be branched, i.e., have a plurality of arms. In some embodiments, the monomers and/or macromers may be multi-armed. For example, in some embodiments, the polymer may be poly(ethylene glycol), which has four-arms (i.e., PEG-tetra, $PEG_4$). In another embodiment, the polymer may be poly(ethylene glycol), which has six-arms (i.e., $PEG_6$). In yet another embodiment, the polymer may be poly(ethylene glycol), which has eight arms (i.e., PEG-octa, $PEG_8$).

Similarly, each arm comprising a polymer, such as the poly(ethylene glycol), may have a different molecular weight. In some embodiments, each arm of the water-soluble polymer may have an average molecular weight of from about 200 daltons to about 35,000 daltons. In another embodiment, each arm of the water-soluble polymer may have an average molecular weight of from about 15,000 daltons to about 35,000 daltons. In yet another embodiment, each arm of the water-soluble polymer may have an average molecular weight of from about 2,000 daltons to about 15,000 daltons. In a further embodiment, each arm of the water-soluble polymer may have an average molecular weight of from about 200 daltons to about 2,000 daltons.

In some embodiments, exemplary monomers and/or macromers for use in making the microparticles include eight arm PEG-octavinylsulfone ($PEG_8$-VS), eight arm PEG-octaamine ($PEG_8$-Amine), four arm PEG-tetraacrylate ($PEG_4$-Ac) and eight arm PEG-octaacrylate ($PEG_8$-Ac). Each arm consists of a linear PEG with one end attached to a core molecule (e.g. hexaglycerol) and the other end containing the listed functional group.

In another embodiment of the present disclosure, the macromers and/or monomers comprise greater than about 75% by weight poly(ethylene glycol) or poly(vinyl pyrrolidone).

(b) Cross-Linking Agents and Functional Groups/Agents

The cross-linking agent (or agents) and/or functional agents used to make the microparticles of a cross-linked polymer may be a small molecule (such as, e.g., dithiothreitol), a peptide, a protein, a linker molecule, a biomolecule, or mononers/macromers of a water-soluble polymer. Non-limiting examples of peptides, proteins, or biomolecules that may be used as cross-linkers and/or functional agents include, but are not limited to, lipid-binding proteins (e.g., bovine serum albumin (BSA), lipoproteins (e.g., high density lipoproteins such as Apo A-I, Apo B-48, or Apo B-100), RGD peptides, protease-degradable peptide linkers (e.g., plasmin degradable peptides), heparin-binding proteins, growth factors (e.g. GDNF), fusion proteins (e.g., proteins containing glutathione S-transferase (GST) tags, FLAG tags, or biotin tags), enzymes (e.g., chondroitinase, sphingosine kinase), antibodies, and cell adhesion proteins (e.g., laminin). Cross-linking agents may be used to subsequently include therapeutic molecules or other functional agents in the microparticles via affinity interactions. The affinity interactions may be mediated by antigen-antibody interactions, biotin-avidin interactions, small molecule-protein interactions, and the like. Exemplary therapeutic molecules/functional agents include pharmaceutically active agents, heparin, glutathione, lipids, growth factors, laminin, and other bioactive agents.

The cross-linking agent suitably has a functionality of greater than 2. In some embodiments, the water-soluble polymers themselves may be considered a cross-linking agent if they have a functionality greater than 2. The cross-linking agent may have functional groups selected from the group consisting of sulfones, sulfoxides, sulfonates, sulfonamides, maleimides, sulfhydryls, phosphonates, phosphonamides, acrylates, amines, alkynes, azides, isocyanates, halides, hydroxyls, carboxyls, and esters. Those of skill in the art will appreciate that the functional groups of the cross-linking agent will be complementary to the functional groups of the polymer monomers/macromers.

In some embodiments, $PEG_8$-VS may be combined with BSA. In another embodiment, $PEG_8$-VS may be combined with $PEG_8$-Amine. In yet another embodiment, $PEG_8$-Ac or $PEG_4$_Ac may be combined with $PEG_8$-Amine. In other embodiments, $PEG_8$-VS may be combined with plasmin degradable PEG-$(VRN)_8$, where VRN is a plasmin-sensitive peptide having the amino acid sequence valine-arginine-asparagine. In additional embodiments, $PEG_8$-VS may be combined with clickable $PEG_8$-Azide/Amine and/or $PEG_8$-Cyclooctyne/Amine. $PEG_8$-Azide/Amine and $PEG_8$-Cyclooctyne/Amine may be added to separate batches of a degradable microsphere precursor solution ($PEG_8$-VS./PEG-$(VRN)_8$) at a 1:50 molar ratio of clickable PEG to all other PEG as further described below. The ratio of functional groups of the monomers/macromers to the functional groups of the cross-linking agent(s) may range from about 1:0.2 to about 1:4.

The complementary functional groups of the monomers/macromers and cross-linking agent(s) react to form covalent bonds, thereby forming the cross-linked polymer. In some embodiments, the polymerization is a condensation polymerization. The bonds formed between the monomers/macromers and cross-linking agent(s) may be essentially non-degradable or they may by degradable. In some embodiments, the bonds may be degradable by hydrolysis. For example, the ester linkages between $PEG_8$-Am and $PEG_4$_Ac or $PEG_8$-Ac may be hydrolyzed in water within two days under physiological conditions. In another embodiment, the bonds may be enzymatically degradable. The bonds may be degraded by proteases, such as matrix metalloproteinases, plasmin or other enzymes. The microparticles formed by the process generally comprise unreacted functional groups that may be used in downstream applications (e.g., attaching biologically active molecules or making scaffolds).

Figure 1B:
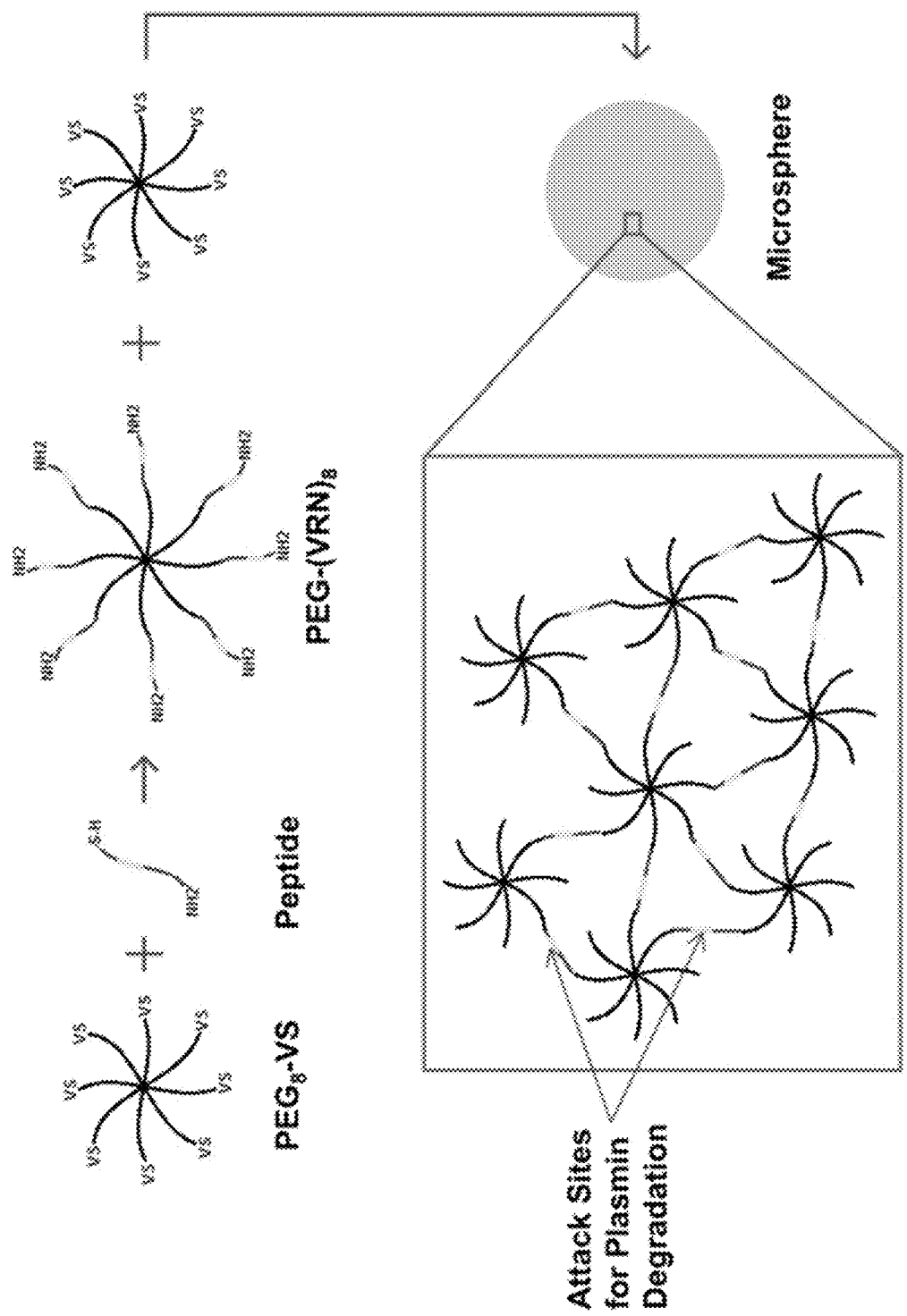
FIG. 1B shows the production of plasmin degradable microparticles through the formation of PEG-(VRN)$_8$, where VRN is a plasmin-sensitive amino acid sequence valine-arginine-asparagine.
Figure 1C:
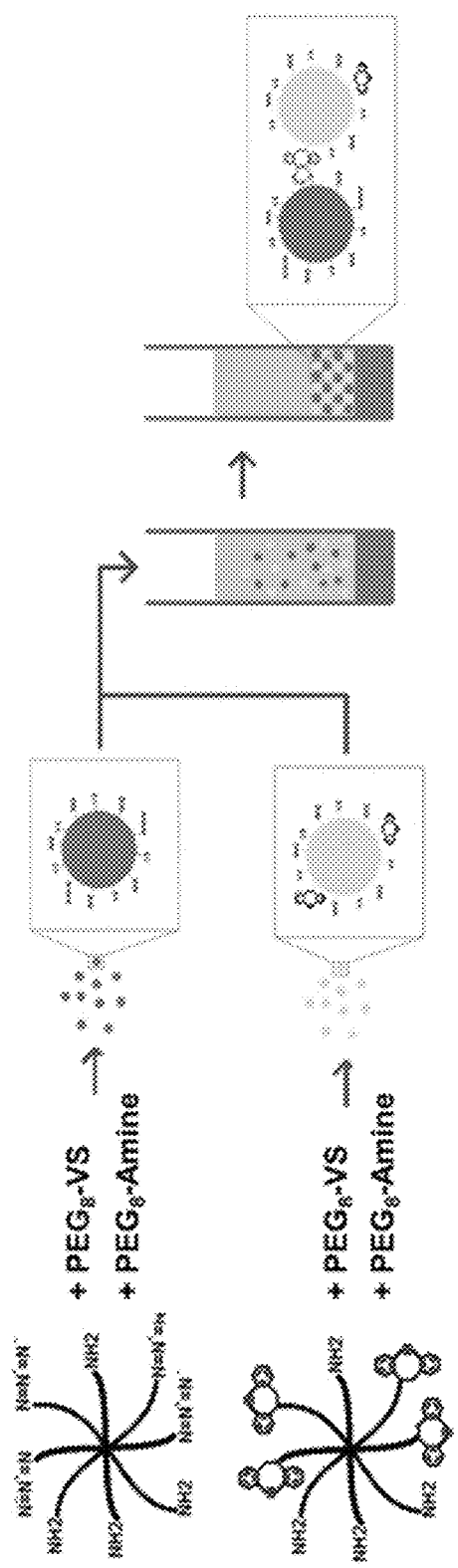
FIG. 1C shows scaffold formation through addition of 'Click' cross-linking agents. PEG$_8$-Azide/Amine and PEG$_8$-Cyclooctyne/Amine were added to the microparticles during formation producing batches of microparticles decorated with either azide or cyclooctyne groups. Upon mixing and centrifugation, the click agents will react to one another, covalently coupling the microparticles together to form a scaffold.

FIG. 1 shows chemistries for addition of various biological functionalities. In various aspects, a plasmin sensitive peptide sequence may be incorporated into the microparticles, as seen in FIG. 1B. In one aspect, the peptide sequence Ac-GCGGVRNGGK—$NH_2$ may be used to allow migrating Schwann cells and/or extending axons to degrade a scaffold within a nerve guidance conduit (NGC). The N-terminus and C-terminus of the peptide may be acetylated and amidated, respectively, to prevent any unwanted cross-linking during microparticle formation. The peptide may contain a thiol group, for example on a cysteine residue that reacts rapidly with vinyl sulfone groups on $PEG_8$-VS. By combining the peptide with $PEG_8$-VS in a ratio of one peptide chain to every vinyl sulfone group, an eight-arm PEG with arms terminated with plasmin-sensitive peptides may be created (PEG-$(VRN)_8$). The lysine at the C-terminal end of the peptide contains a primary amine group, effectively producing a type of plasmin-degradable $PEG_8$-Amine. Alternatively, the peptide $H_2$NGGVRNGGC-$NH_2$ would also be acceptable, as it contains a single primary amine, a single thiol, separated by the plasmin sensitive sequence. Because of the stepwise nature of the chemical scheme, any cross-linkages between PEG molecules in the microparticles may be vulnerable to attack by plasmin. To form microparticles, PEG-$(VRN)_8$ and $PEG_8$-VS may be added at a 1:1 M ratio and reacted as the previous $PEG_8$-Amine/$PEG_8$-VS constituents were. Producing microparticles may further include a pre-incubation step, in which undiluted PEG-$(VRN)_8$ and $PEG_8$-VS (200 mg/mL total PEG) may be incubated for greater than about 30 min at about 37° C. before dilution in 0.6 M sodium sulfate and subsequent incubation at about 70° C. In one aspect, PEG-$(VRN)_8$ and $PEG_8$-VS may be incubated for about 1 h at 37° C. The incubation time at 70° C. in the phase separated state may determine the extent of crosslinking within the microparticle, affecting its swelling, buoyancy and the rate of diffusion of proteins through the material. Because the time in the phase separated state may control the rate of release of growth factor or rate of microsphere degradation, this time length may be carefully monitored during microparticle formation.

In some embodiments of the present disclosure, the affinity interaction is mediated by antibodies, heparin or heparin-binding peptides. In an aspect, an intermediate step of bonding cysteine to the heparin through the EDC/NHS activation of carboxyl groups may be used. This method of heparin attachment may provide better control over the extent of the reaction, minimization of heparin self-cross-linking, higher reproducibility, and increased incorporation of heparin. Although both the amine and thiol on cysteine may react with NHS-activated carboxyls on heparin, the neutral conditions may favor an S-to-N acyl shift leaving a free thiol. The amount of cysteine conjugated to the heparin may be quantified by an Elman's assay for the thiols on the pendant cysteines (free cysteine would be readily removed in the dialysis step). This "thiolated heparin" may then be reacted with $PEG_8$-VS in a controlled manner using EDC/NHS activated carboxyl groups reacted with $PEG_8$-Amine directly (reproducibility of the EDC/NHS activation is challenging due to fast reaction kinetics, age of the EDC, and inability to quantify activation extent during each reaction). In this aspect, microparticles with as much as 21% by weight heparin content may be created. However, in other aspects, higher amounts of heparin may inhibit, and sometimes even prevent, the formation of microparticles by changing the solubility characteristics of PEG in 0.6 M sodium sulfate. Microparticles formed at the high heparin conditions may be much smaller (for example, less than about 1 micron in diameter) than microparticles without high amounts of heparin (about 5-20 microns). In an aspect, the thiolated heparin may be reacted to $PEG_8$-VS after the microparticles have been formed (thiolation chemistry shown in FIG. 1A). In various aspects in which thioloated heparin is reacted with microparticles, the heparin content of the microparticles may range from about 3% to about 6% by weight. In one aspect, the heparin content of the microparticles may be at least about 3% by weight or at least about 4% by weight.

In an aspect, cell adhesion functionality may be added to the microparticles via covalent attachment of laminin to the microparticles. Free thiols or amines on laminin may attach to PEG via vinyl sulfone groups. To attach laminin to microparticles, laminin (20 mg/mL) may be added to previously formed and washed microparticles and incubated overnight at room temperature. For example, $PEG_8$-Amine/

Figure 2A:
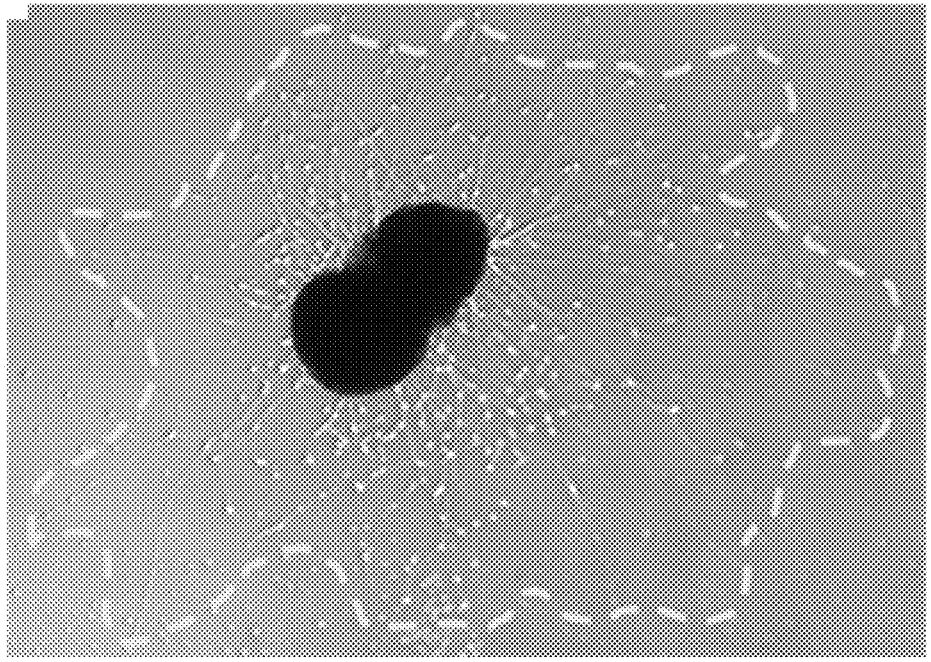
FIG. 2A shows typical DRG growth on PEG$_8$-VS/PEG$_8$-Amine gels decorated with laminin at 20 mg/mL (2 days after seeding, dashes show border of growth).
Figure 2B:
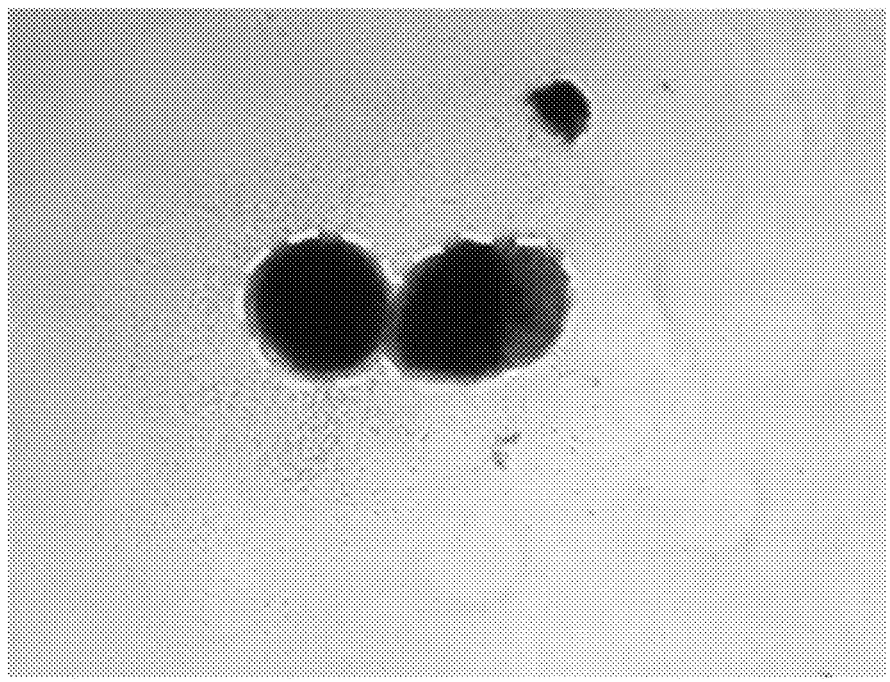
FIG. 2B shows DRG growth on PEG$_8$-VS/PEG$_8$-Amine gel without laminin. (2 days after seeding, dashed lines show border of growth).
Figure 2C:
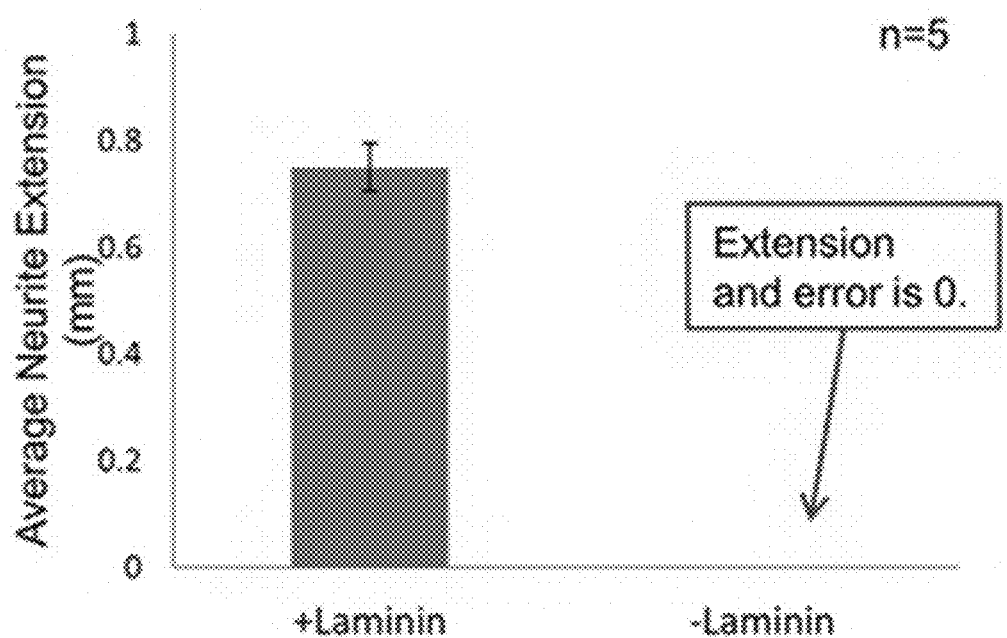
FIG. 2C shows average neurite extension in mm for DRG's cultured on PEG gel with and without laminin (n=5). No growth was observed in DRG's without laminin present. Error bars shown but equal to 0 for the -laminin condition.
Figure 3A:
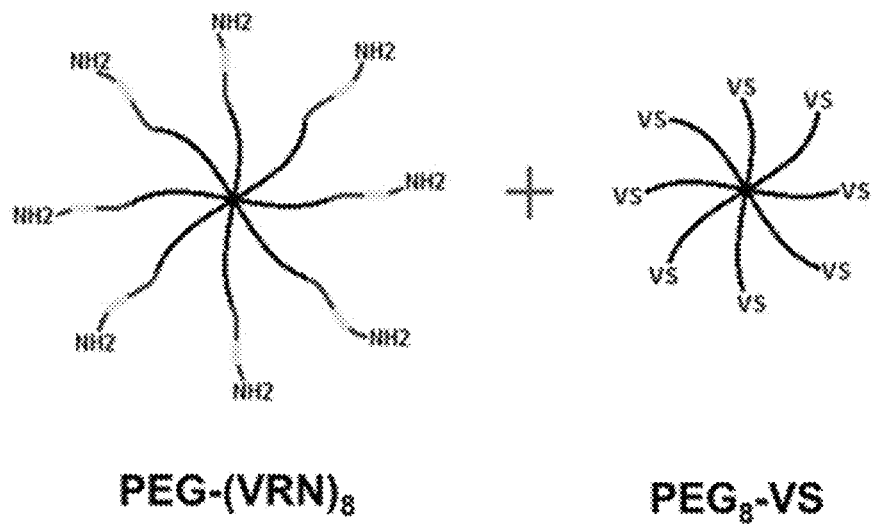
FIGS. 3A-3F illustrate a final functionalized microparticle procedure.
Figure 3B:
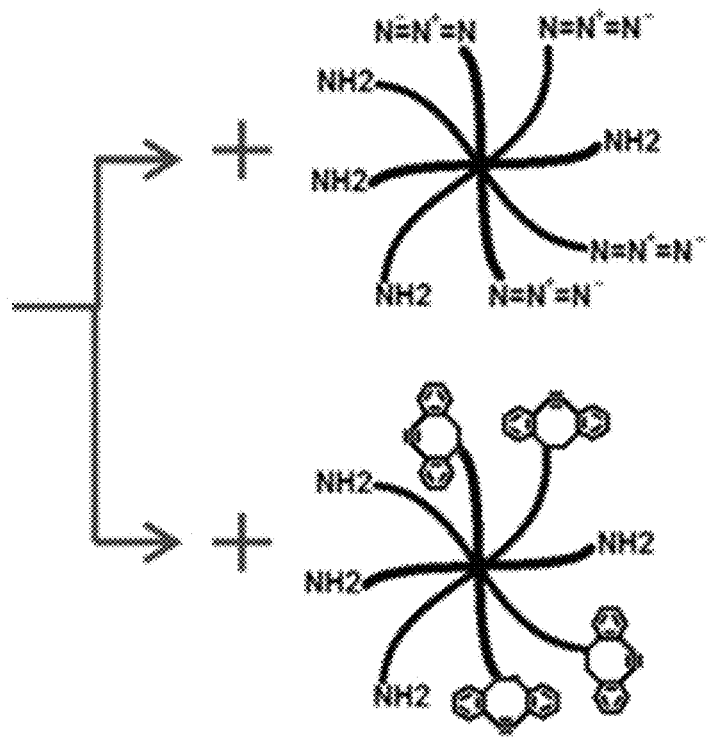
Figure 3C:
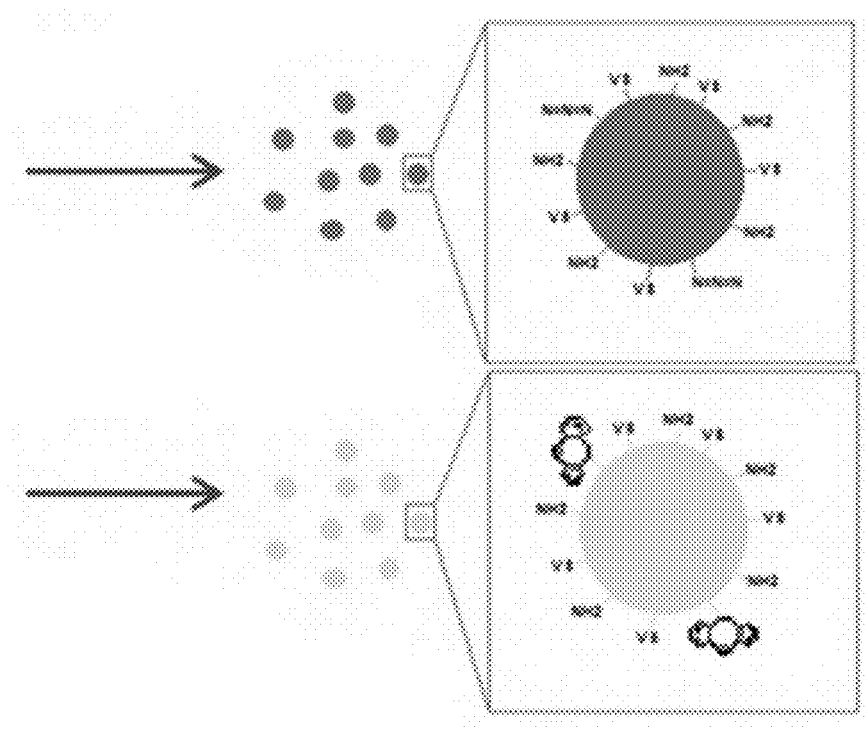
Figure 3D:
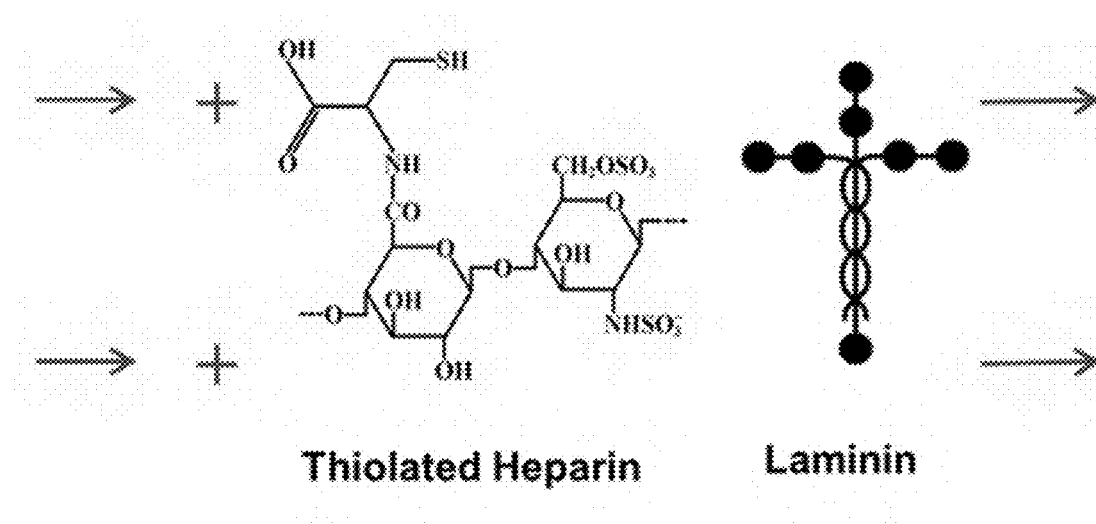
Figure 3E:
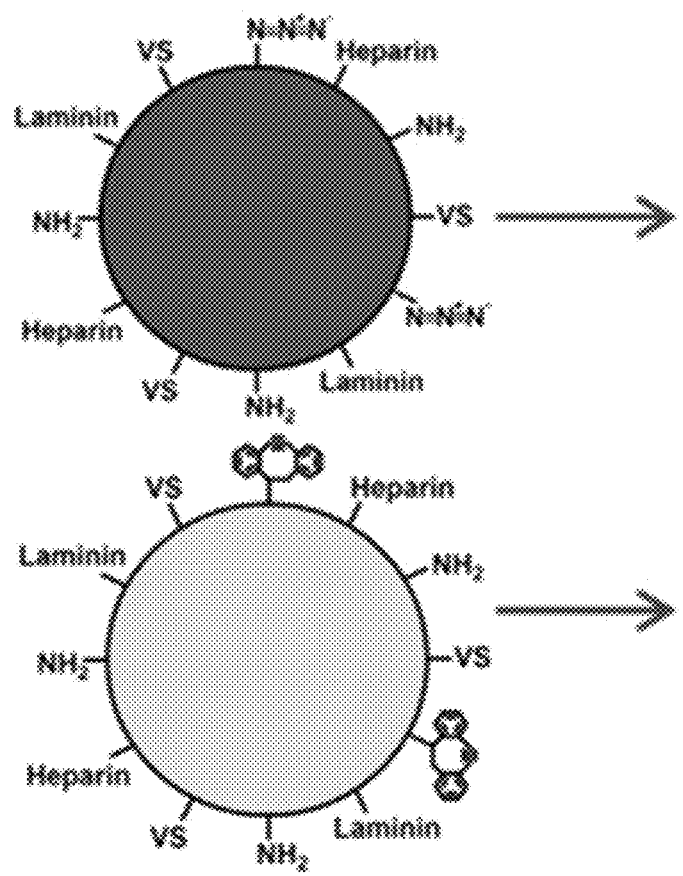
Figure 3F:
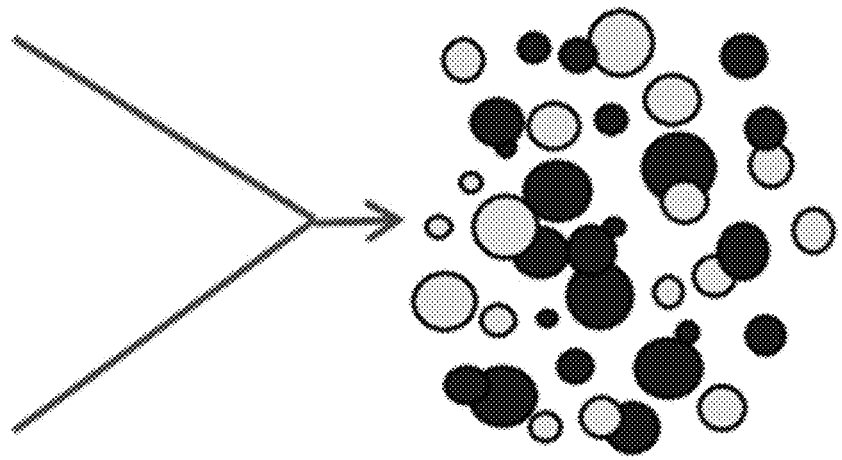

PEG$_8$-VS may be incubated overnight with laminin (20 mg/mL) at 37° C., allowing the cysteines or amines on laminin to react with free vinylsulfones, covalently coupling the laminin to the microparticles. In one aspect, the laminin on the microparticles may encourage neuronal growth within the scaffold. FIG. 2 shows DRG's cultured on the gels with laminin compared to gels without laminin. FIG. 2. shows that laminin covalently attached to PEG hydrogels promotes growth of DRG's. DRG's cultured on PEG gels without laminin showed no growth. DRG's cultured on PEG gels with laminin extended neurites.

(c) Clickable PEG-Microparticles

Figure 10A:
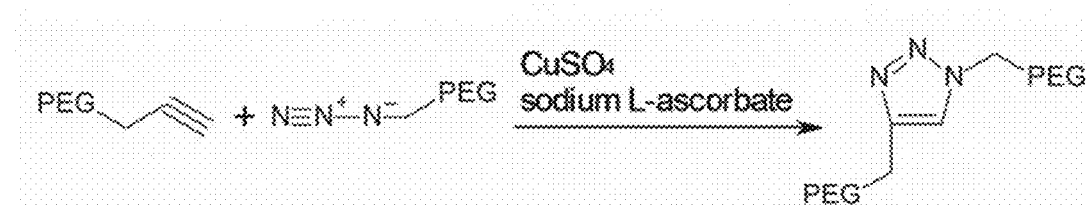
FIG. 10A shows clickable PEG derivatives were reacted using copper(I)-catalyzed azide—alkyne cycloaddition.
Figure 10B:
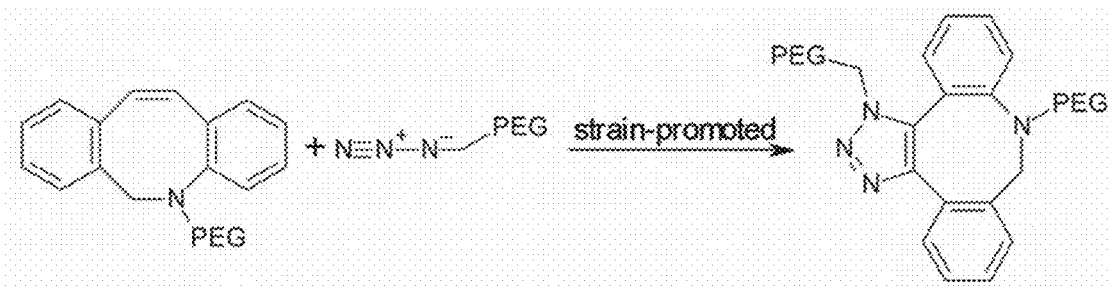
FIG. 10B shows clickable PEG derivatives were reacted using strain-promoted Huisgen 1,3-dipolar cycloaddition between azides and alkynes.
Figure 10C:
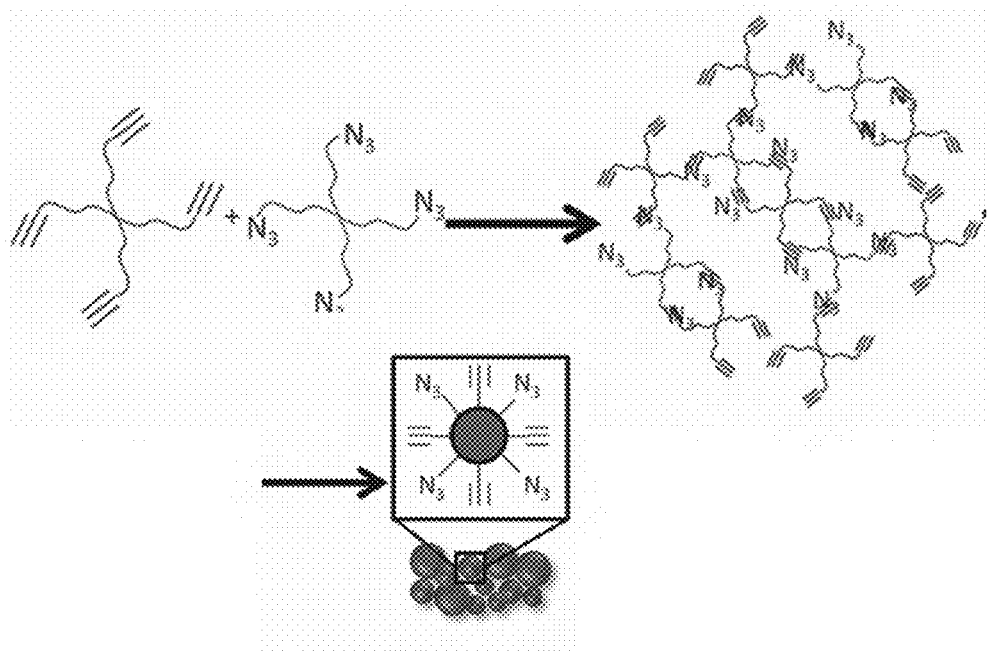
FIG. 10C shows that in the presence of sodium sulfate, four-arm clickable PEG derivatives phase-separated and reacted to form highly crosslinked hydrogel microparticles. These microparticles contain residual reactive groups that allowed further crosslinking.

In an aspect, "clickable" microparticles may be formed using copper(I)-catalyzed or copper-free azide—alkyne cycloadditions. For the copper(I)-catalyzed reaction, PEG-azide may be mixed with PEG-alkyne, which may be synthesized by the reaction of PEG-amine with propiolic acid. Reaction of PEG-azide with PEG-alkyne to form a bulk hydrogel at 37° C. may require the addition of Cu(II) SO$_4$ and sodium L-ascorbate (FIG. 10A); however, some reaction may occur without copper at about 95° C. For the copper-free reaction at 37° C., PEG-azide may be mixed with PEG-cyclooctyne (FIG. 10B). The latter may be synthesized by reaction of PEG-amine with a commercially available carboxyl-derivatized aza-dibenzocyclooctyne. In both the copper(I)-catalyzed and copper-free reactions, each PEG derivative may serve as a potential crosslink site, forming highly crosslinked hydrogel networks upon reaction (FIG. 10C). Reactive groups on the PEG monomers that are not consumed during microparticle formation should still be available for subsequent addition of biologically active molecules or further intraparticle or interparticle crosslinking, the latter of which can be used for "bottom-up" scaffold assembly (FIG. 10C).

Figure 10D:
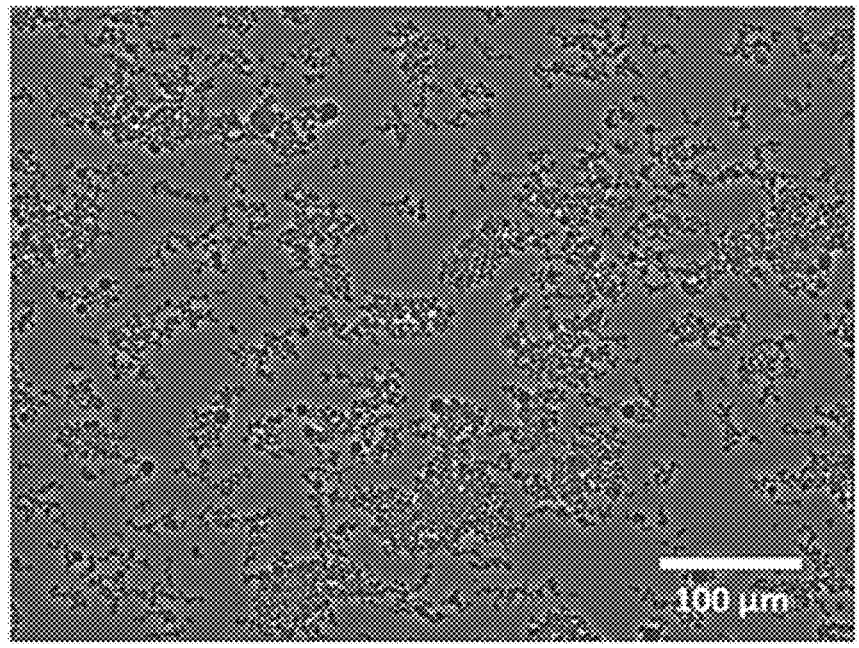
FIG. 10D shows microparticles formed using copper(I)-catalyzed azide—alkyne cycloaddition. These microparticles were formed by inducing phase separation in $325 \times 10^{-3}$ M sodium sulfate upon heating to 37° C. for 2 min.
Figure 10E:
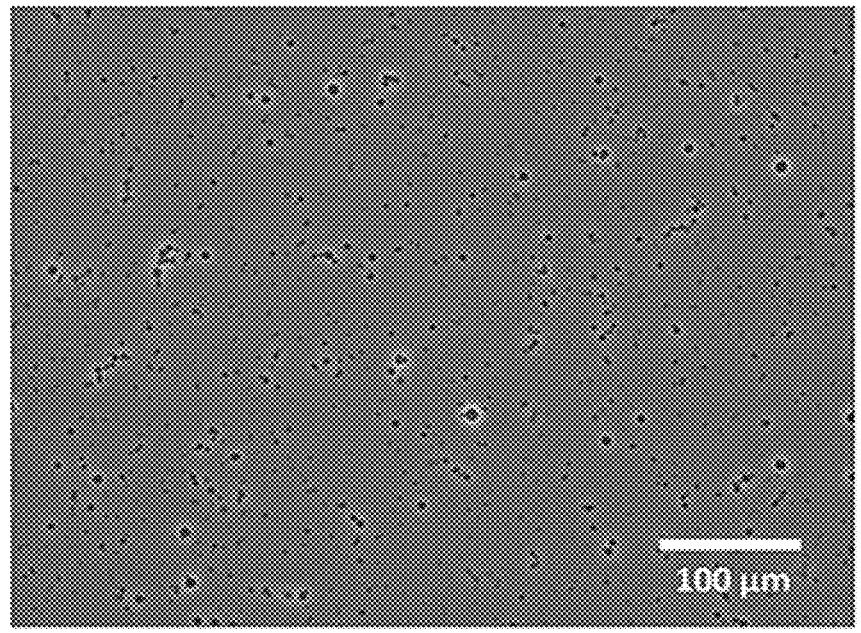
FIG. 10E shows microparticles formed using strain-promoted azide-aza-dibenzocyclooctyne cycloaddition. These microparticles were formed by inducing phase separation in $250 \times 10^{-3}$ M sodium sulfate upon heating to 37° C. for 2 min.

To produce microparticles, the clickable PEG derivatives may be reacted in the phase-separated state. Small microparticles (1-10 μm) may be generated in the presence of sodium sulfate for both the copper(I)-catalyzed reaction (FIG. 10D) and the copper-free reaction (FIG. 10E). To form these small microparticles, the concentration of sodium sulfate may be chosen such that phase separation does not occur at room temperature, allowing mixing of the reagents prior to the thermally induced phase separation. With the copper(I)-catalyzed reaction, about $325 \times 10^{-3}$ M sodium sulfate may result in phase separation upon heating from room temperature to 37° C. Microparticles may be formed after about 2 min. For the copper-free reaction, a concentration of about $250 \times 10^{-3}$ M sodium sulfate may be used for the formation of small microparticles. The lower concentration of sodium sulfate may be required because the LCST of PEG is depressed by the presence of the hydrophobic dibenzocyclooctyne on the PEG. Microparticles may also be formed by substituting the sodium sulfate with dextran or polyacrylamide (MW=$5 \times 10^6$-$6 \times 10^6$ Da). Both of these polymers form aqueous two-phase systems with PEG.

Figure 10F:
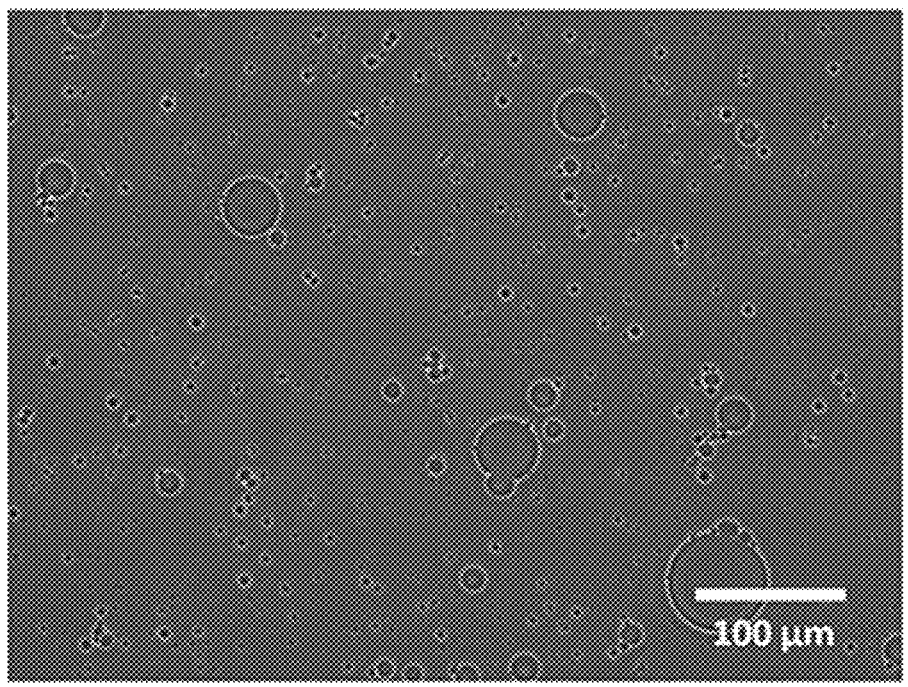
FIG. 10F and FIG. 10G show larger microparticles may be formed with the strain-promoted cycloaddition by inducing immediate phase separation at room temperature (25° C.) with $500 \times 10^{-3}$ M sodium sulfate, mixing the solution by pipetting three times, and heating to 37° C. for 2 min. Mixing in the phase-separated state resulted in the formation of much larger microparticles due to enhanced coalescence of PEG-rich domains prior to gelation.
Figure 10G:
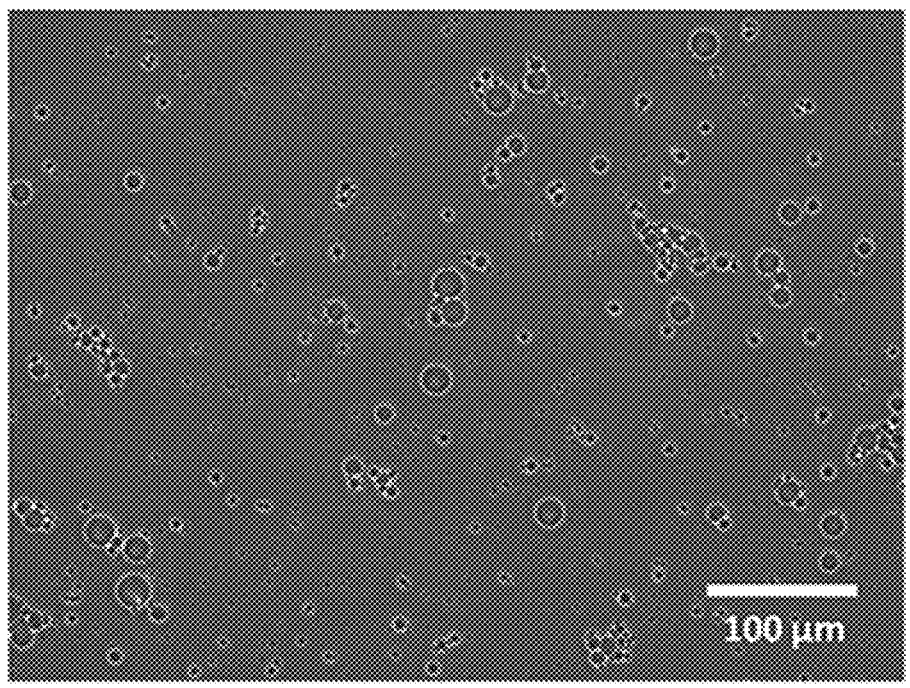

With PEG-cyclooctyne, much larger microparticles (e.g., diameters of about 50 μm or greater) may be formed if higher sodium sulfate concentrations are used. Higher sodium sulfate concentrations may cause phase separation of the PEG derivatives at room temperature, and mixing of the reagents may result in the formation of larger droplets, presumably by flow-induced acceleration of coalescence (FIGS. 10F and 10G). The combination of large and small microparticles may produce stronger materials than those formed from particles of uniform size. The small microparticles may be formed in the absence of mixing as previously described.

In an aspect, the copper(I)-catalyzed reaction may produce microparticles less than about 5 μm in diameter. A high concentration of sodium sulfate ($650 \times 10^{-3}$ M Na$_2$SO$_4$) may only produce small microparticles with the copper(I)-catalyzed system. Changes in the copper concentrations may not affect microparticle size. Increases in the reaction temperature may also not affect microparticle size. This is somewhat surprising as faster reaction kinetics should result in smaller microparticles. Without being limited to a particular theory, it is possible that the copper ions prefer the PEG-poor phase, such that a precipitation polymerization occurs in this phase, and very little crosslinking occurs in the PEG-rich droplets.

In an aspect, PEG$_8$-Amine may be first reacted so that it is about fifty percent substituted with either azide or cyclooctyne groups (PEG$_8$-Azide/Amine and PEG$_8$-Cyclooctyne/Amine). Microparticle precursor solutions may be split into two batches, and one batch may be reacted with PEG$_8$-Azide/Amine while the other may be reacted with PEG$_8$-Cyclooctyne/Amine, with the amines on the clickable PEGs reacting with residual vinylsulfones on PEG-VS in the microparticles. This may result in the production of batches of microparticles decorated with either azide or cyclooctyne groups. Upon mixing these two types of microparticles together, the clickable groups may react to one another, allowing covalent coupling between microparticles to produce a scaffold (see FIG. 1C). In an aspect, the clickable PEG content may be relatively low so as not to hinder plasmin degradability (50:1 non-clickable PEG:clickable PEG molar ratio). At this level, scaffold formation may be relatively slow (over the course of about a few days). However, when implanted in vivo the scaffolds may be in place for weeks, so the click cross-linking functionality may be advantageous. In various aspects, the rate of scaffold formation may be enhanced by centrifuging microparticles such that they are in closer contact, or phase-separating the microparticles with sodium sulfate or dextran and allowing them to become close-packed as a distinct phase-separated layer. In another aspect, use of linear clickable PEG reagents (cyclooctyne-PEG-amine and azide-PEG-amine) may allow better control of the rate of surface erosion by plasmin due to the absence of additional crosslinking between multiple amines in PEG$_8$-Azide/Amine or PEG$_8$-Cyclooctyne/Amine and multiple vinylsulfones within a microsphere.

(d) Process of Forming Microparticles

Forming microparticles of a cross-linked water-soluble polymer or polymers may include combining monomers and/or macromers of at least one water-soluble polymer with at least one cross-linking agent in a solvent that consists essentially of water. At least one of the polymers may have a lower critical solution temperature (LCST) of greater than about 37° C. in water. The mixture of monomers/macromers and cross-linking agent(s) reacts with each other to form the cross-linked polymer. The process may further include polymerizing (e.g., coacervation polymerizing) the cross-linked polymer at a temperature that is above the LCST of the polymer whose LCST is greater than about 37° C. (in water) to form the microparticles of the cross-linked water-soluble polymer. One step in the process can be timing the pre-reaction so that the gel point of the macromonomers occurs at a time that is short relative to the complete phase separation of unstirred solutions following thermally induced phase separation. Another aspect is limiting the cross-linking of the polymer that remains in the solvent-rich phase to avoid precipitation polymerization by increasing the concentration of salt or polymer that is causing the phase separation. In another aspect, precipitation polymerization is encouraged, by ensuring that none of the acromonomers has a lower critical solution temperature (LCST) of greater than about 37° C. in water, but with salt or polymer concentrations chosen such that the reacted macromonomers have an LCST greater than 37° C. in water.

The monomers/macromers and cross-linking agent(s) are combined in a solvent consisting essentially of water. That is, in some embodiments of the present disclosure, the solvent is devoid of surfactants, dispersants, emulsifiers, phase separation agents, and organic solvents. For example, the process can be substantially free of a surfactant or a solvent other than water. The solvent may further comprise salts (i.e. ions). For example, the aqueous solvent may comprise physiological concentrations of salts (e.g., 130-150 mM of sodium/potassium chloride). The salts may be in a polymer form, e.g. a polyelectrolyte (e.g. poly(acrylic acid)). The solvent may further comprise water-miscible solvents such as alcohols that affect the phase behavior of the reactive polymer. The solvent may further comprise other uncharged polymers or osmolytes (e.g. dextran or glycerol) that affect the phase behavior of the reactive polymer.

During the polymerization process, the molecular weight of the cross-linked polymers increases until one molecule grows to fill a large portion of the volume of the original solvent. Thus, during the course of the cross-linking process, a distribution of larger and larger molecular weights of cross-linked polymers may be found. In particular, dynamic light scattering may be used to reveal the presence of large polymers prior to the gel point (i.e., the point at which an infinite polymer network first appears). Dynamic light scattering, thus, may be useful in determining how close to the gel point the reaction has proceeded, and this data may be used to guide the timing of the phase separation process.

The process can further comprise phase separating the partially cross-linked polymer solutions as a coacervate by adjusting the temperature of the reaction such that it is above the LCST of the polymer whose LCST is greater than 37° C. (in water). The time it takes to reach the gel point may be decreased by increasing the temperature. The cross-linking reaction may be allowed to proceed at one temperature below the cloud point for a period of time, or until a certain average size of cross-linked polymers is reached, as judged by light scattering. For example, the cross-linking reaction may be allowed to proceed at about 37° C. for several hours (i.e., about 3-5 h) to many hours (i.e., about 18-24 h). However, it is also possible to mix the monomers/macromers and cross-linking agent(s) and then immediately heat the mixture to above the LCST of the polymer whose LCST is greater than 37° C. (in water). In both cases, the cross-linked polymers that are detectable by light scattering will generally be present prior to phase separation or microparticle formation, as the cross-linking reaction may proceed at some rate between the time the reactive polymers are mixed and the time at which phase separation occurs. Thus, the time remaining until the gel point is reached generally will depend on the temperature history. Even if the components are mixed and the mixture is immediately heated above the LCST, it still may take a certain period of time before the mixture actually heats up to the target temperature, and because the elevated temperature will increase the rate of the reaction, the reaction will possibly reach an advanced degree of cross-linking before the LCST is crossed.

The pH may also affect the speed of reaction. Thus, the cross-linking reaction may be allowed to proceed for shorter times or longer times at a pH different from physiological pH (pH=7.4), particularly if one of the components contains pH-sensitive reactive groups. For example, PEG microparticles formed at pH 5.0 are larger in size than PEG microparticles formed at pH 8.0 if formed using PEG-amine. The pH of the coacervation reaction may range from about pH 3 to about pH 10, or more preferably from about pH 5 to about pH 8. One factor in the process is thus the ability to predict and/or measure and thus control the time remaining until gelation.

While mixing may hasten phase separation into two distinct layers of fluid, some small amount of mixing prior to gelation may be used to produce larger microparticles. The reacting components may be phase separated individually and then mixed, however the mixing step may affect coarsening and thus microparticle size. In one emulsion process known in the art, the solutions were allowed to substantially phase separate and then were vigorously agitated in an attempt to produce spherical droplets. With PEG and magnesium sulfate, this produced large aggregates of microparticles following free radical polymerization. Stirring was thus unable to prevent coarsening on the time scale of cross-linking. This was attributed to the low viscosity of the solution, which potentially led to rapid coarsening. This illustrates that the kinetics of cross-linking should be well matched to the kinetics of coarsening. If the amount of mixing or agitation of the solution leads to an acceptable increase in the coarsening rate, mixing and agitation may also be used in the process. However, to prevent aggregation of particles, one can halt mixing prior to reaching the gel point.

In another embodiment of the present disclosure, increasing the ionic strength of the aqueous solvent may decrease the LCST. Ionic strength may be adjusted by the addition of sodium sulfate, sodium phosphate, magnesium sulfate, potassium sulfate, potassium chloride, potassium bromide, and the like. That is, in some embodiments, the LCST is decreased by increasing a concentration of ions in the solvent. The concentration of ions may be added during combination of the macromers and/or monomers in a sufficient amount to decrease the LCST. The concentration of additional ions may be at least about 300 mM, at least about 400 mM, at least about 500 mM, or at least about 600 mM. As shown in the examples, 600 mM sodium sulfate reduces the LCST of PEG to less than 37° C. if the end groups are not hydrophilic. Additionally, temperatures much higher than the LCST may be utilized, reducing the duration of time required to produce microparticles. For example, 70° C. for 8 min can be sufficient for PEG microparticle formation in the presence of 600 mM sodium sulfate. In general, the higher the temperature, the shorter the time until microparticle formation is complete.

Ionic strength can affect the rate of coarsening in that higher salt concentration can lead to a greater difference in the densities of the two phases. The phases more rapidly separate due to the large density difference, requiring a faster rate of reaction. Thus, an optimal range of salt concentrations may exist. An exemplary salt concentration is 0.6 M sodium sulfate in PBS for coacervation polymerization of $PEG_8$-VS and $PEG_8$-Amine to form microspheres. At this salt concentration, the solution is not phase separated at room temperature, allowing mixing of the components without affecting coarsening. However, the solution becomes phase separated above about 37° C. Other PEG derivatives will have different LCST behavior and will have different optimal salt concentrations. To carry out a precipitation polymerization of PEG-diacrylate by photopolymerization, 0.54 M sodium sulfate in PBS is desirable. At this salt concentration, PEG-diacrylate is soluble during photoinitiated free radical polymerization at room temperature. However, the polymerized product is not water-soluble at this salt concentration, limiting the size of polymerized domains, leading to a precipitation polymerization. While a precipitation polymerization and coacervation polymerization can occur simultaneously, they are distinct processes, distinguished by the solubility of the macromonomer at the polymerization temperature (all macromonomers soluble in a precipitation polymerization, some or all macromonomers insoluble in a coaccervation polymerization).

The distance between the cross-links can generally affect the mechanical properties of a microparticle. The distance between cross-links may be adjusted by using polymers of different molecular weights. The distance between cross-links may also be varied by halting the reaction before maximal cross-linking. As a result, microparticles may be formed that vary in stiffness. This may be useful in producing homogenous materials with specific mechanical properties or permeability to solutes, or in forming materials with gradients in mechanical properties or permeability.

Figure 16A:
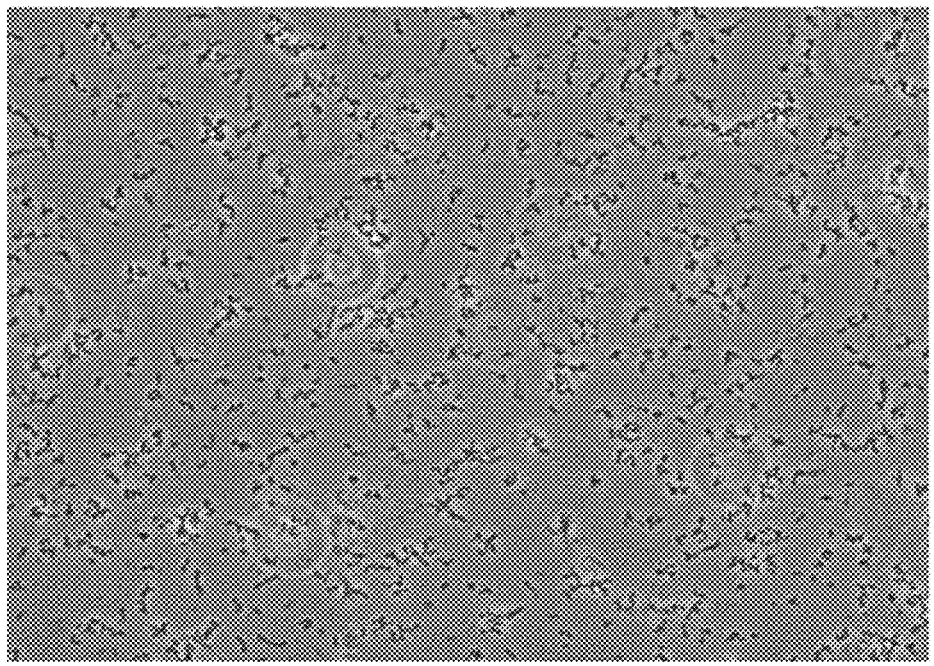
FIG. 16A and FIG. 16B present microparticles formed by photopolymerization of PEG-diacrylate mol. wt. 3400 in 700 mM sodium sulfate.
Figure 16B:
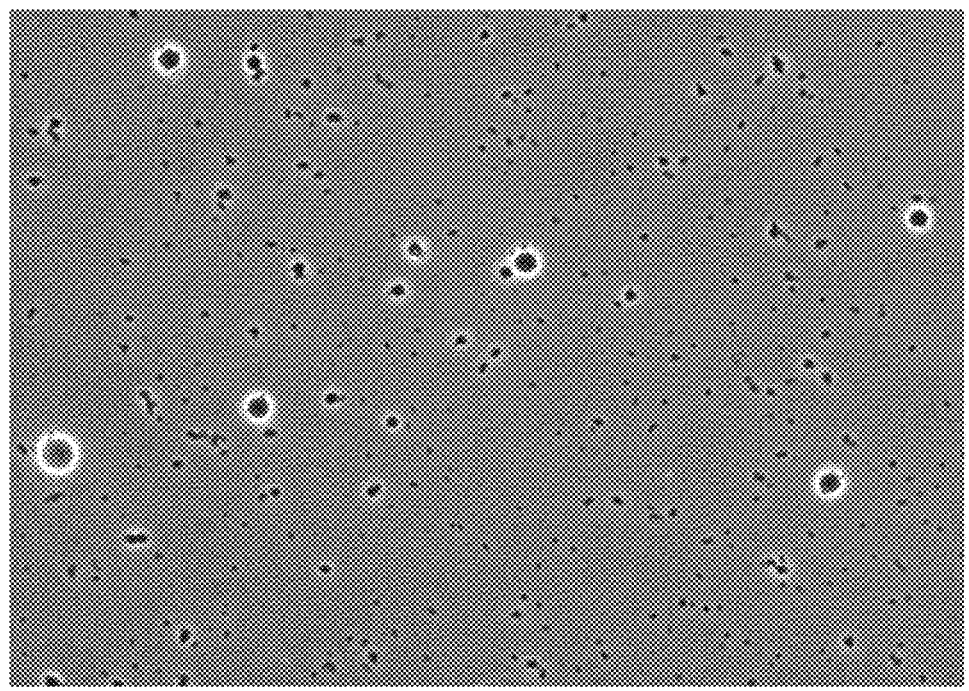

Although the polymer solutions are phase separated, some amount of polymer typically remains in the solvent-rich phase. This can be a hindrance to a successful free-radical polymerization. If the initiator is soluble in the solvent-rich phase, the polymer remaining in the solvent-rich phase can tend to polymerize. This may lead to a precipitation polymerization as the molecular weight of the macromer increases. Polymerization within the polymer-rich phase may also occur, leading to a bimodal distribution of sizes (see, e.g., FIGS. 16A and 16B). By lowering the salt concentration slightly, however, the macromer may be made soluble throughout the polymerization process. Only a true precipitation polymerization occurs, which can result in a monomodal distribution of microparticle sizes.

Figure 4:
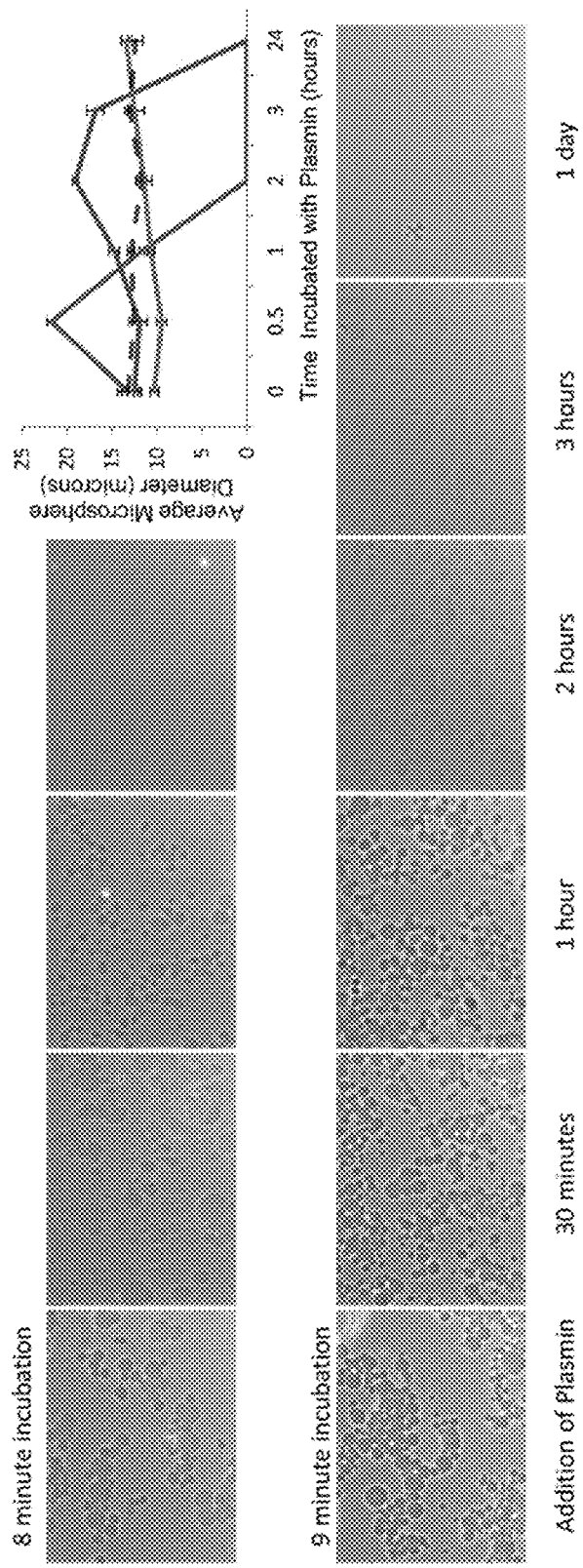
FIG. 4 shows degradation of microparticles suspended in plasmin. Microparticles formed by incubation at 70° C. for 8, 9 or 10 min were suspended in 1 unit/mL of plasmin and incubated at 37° C. to view the rate of degradation. The graph shows average microparticle diameter over time for 8 (blue), 9 (red), and 10 min (green) formation times (i.e. length of incubation in the phase separated state during microparticle formation at 70° C.). Black dashed line indicates 9 min microparticles in control conditions (no plasmin). (n=4).
Figure 5A:
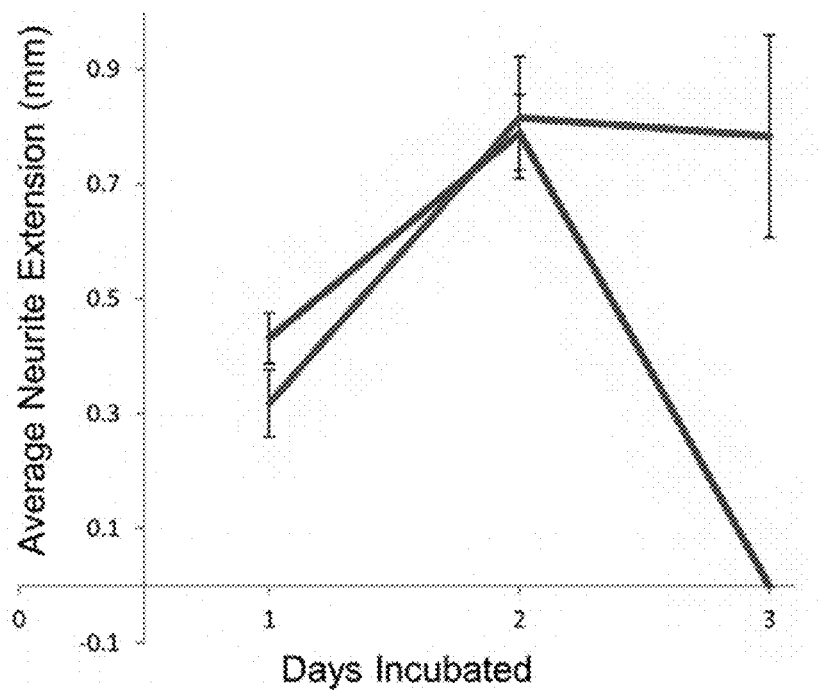
FIG. 5A shows GDNF activity retention for DRG growth. Average neurite extension for DRG's grown on thin, bulk PEG gels with 0.8 mg/mL incubated laminin for one, two, and three days under two media conditions: Microparticle released GDNF (833 ng/mL incubation) in MNB media (Blue line, n=8), MNB media with no GDNF (Red line, n=14).
Figure 5B:
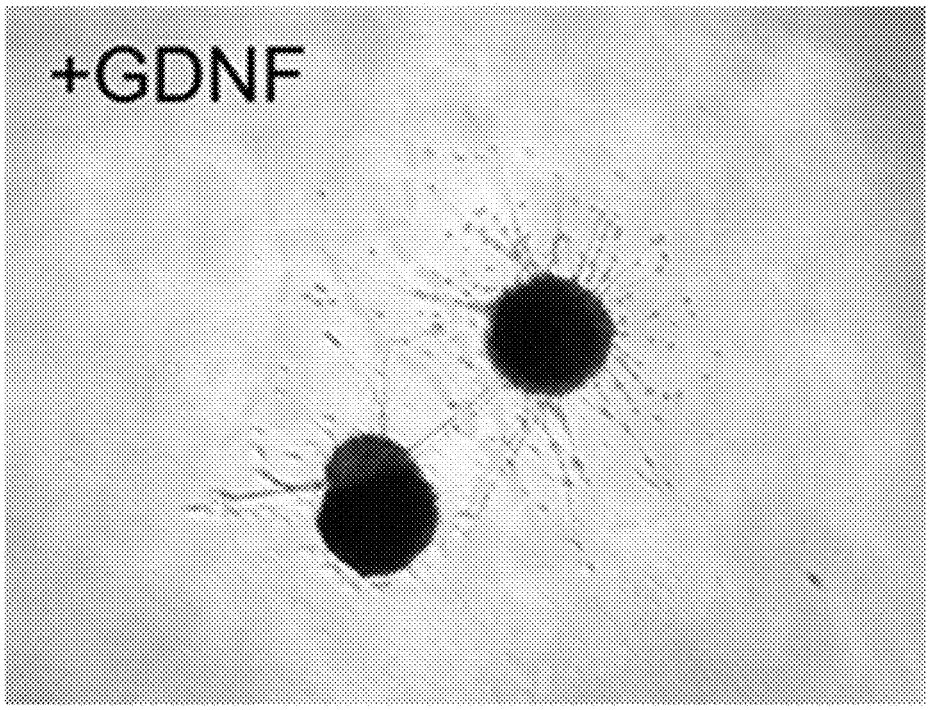
FIG. 5B is a photomicrograph of DRG neurite extension in media with GDNF from the 3 day time point. Yellow dashes indicate boundary of neurite extension.
Figure 5C:
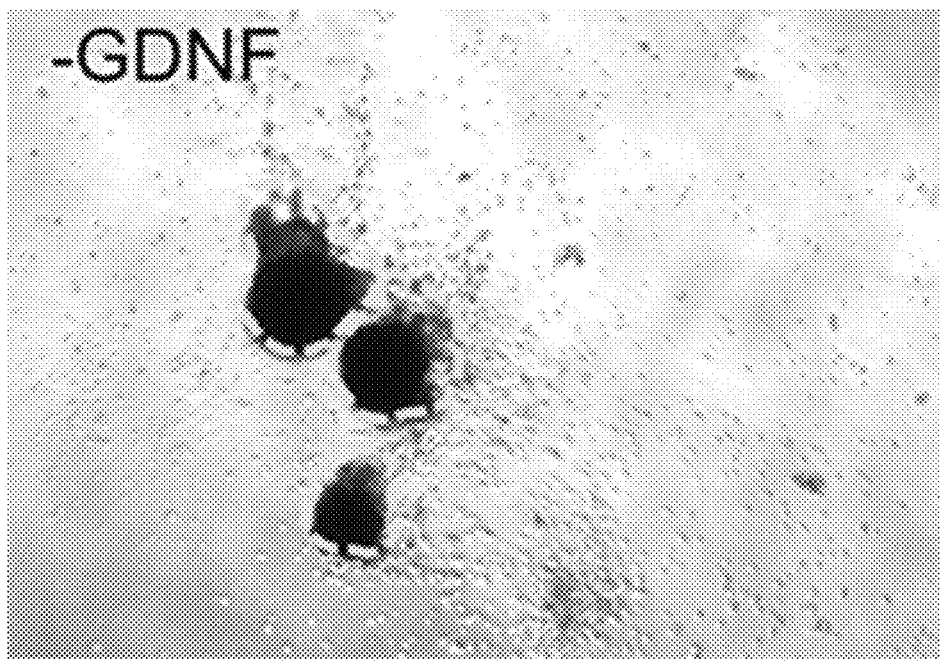
FIG. 5C is a photomicrograph of DRG neurite extension in media without GDNF. All DRG's in the control condition (No GDNF) had no extensions at Day 3. Error bars shown, but error was zero due to uniformity of samples at this condition.

In an aspect, a method for fabricating fully functionalized microparticles is shown in FIG. 3. This method is a combination of the processes and functionalizations discussed above, ending with an about 30 min incubation in about 2.5 mg/mL cysteine to cap any remaining free vinyl-sulfone groups. This capping step may prevent unwanted covalent binding of the microparticles to GDNF (or any other proteins). While the lower amounts of Click reagents (50:1 non-clickable PEG to clickable PEG) may allow for the retention of plasmin degradability, this is only with a particular range of microparticle formation incubation times. For less than about 8 min at 70° C., no microparticles may form. For more than 10 min at 70° C., the microparticles may crosslinked to a degree that eliminate their ability to be degraded by plasmin. Within this range of 8-10 min incubation at 70° C., the rate of degradation may be tunable. In an aspect, microparticles incubated at 70° C. in the phase separated state for less than about 10 min may degrade in a matter of hours, while microparticles incubated for exactly 10 min may degrade over the course of days or not at all in a solution containing high concentration of plasmin (FIG. 4). In vivo, however, axons activating plasmin may degrade the microparticle scaffolds locally, which should take a considerably greater amount of time. Thus, this should represent an accelerated model compared to degradation in vivo. Without being limited to a particular theory, longer times in the phase-separated state may result in additional crosslinks within the material, increasing mechanical stiffness, decreasing swelling in water or buffered water and decreasing enzymatic degradability.

The range of microparticle crosslinking times in the phase separated state may be extended to higher values if linear clickable PEG reagents (cyclooctyne-PEG-amine and azide-PEG-amine) are used instead of multiarm clickable PEG reagents (e.g. $PEG_8$-Azide/Amine and $PEG_8$-Cyclooctyne/Amine). For example, the microparticle crosslinking time may be up to about 45 minutes, the upper time limit when aggregation of microparticles becomes substantial. In various aspects, the microparticle crosslinking time may range from about 8 min to about 9 min, from about 8.5 min to about 9.5 min, from about 9 min to about 10 min, from about 10 min to about 20 min, from about 15 min to about 25 min, from about 20 min to about 30 min, from about 25 min to about 35 min, from about 30 min to about 40 min, and from about 35 min to about 45 min.

The multiarm clickable PEG reagents may introduce non-degradable crosslinks into the microparticles, potentially hindering enzymatic degradation. Linear clickable PEG reagents do not face this limitation. Additionally, a greater amount of linear clickable PEG reagents may be reacted with the microparticles than multiarm clickable PEG reagents because of the absence of the potential for introduction of non-enzymatically cleavable crosslinks.

In another aspect, a linear clickable PEG reagent may be used with the following sequences: (1) clickable group-PEG-degradable peptide-amine, or (2) clickable group-degradable peptide-PEG-amine. The degradable peptide in this reagent may be of different identity from the degradable peptide within the bulk of the microsphere. This may enhance the difference in degradation rates between microparticles versus within microparticles.

II. Modular Scaffolds

A "scaffold" herein refers to a three dimensional object that allows incorporation of living cells within the object, either at the time of formation or by ingrowth of cells in vitro or in vivo. An aspect of the present disclosure is directed to a scaffold comprising hydrogel microparticles. Scaffolds for supporting cell growth are generally known in the art, including two types of microengineered scaffolds: top down and bottom up. Top down scaffolds start with a bulk hydrogel that is made non-homogenous by a variety of patterning methods. Bottom up scaffolds can be produced by assembling hydrogel microparticles, which may or may not contain cells. Microengineered scaffolds are described herein that have favorable properties of both types of scaffolds but fit into neither category. The current scaffolds differ from previous bottom up scaffolds in the intentional gradient in degradability between microparticles versus within microparticles, allowing cells to form pathways for migration. Unlike previous patterned top down scaffolds, the patterning is performed by living cells that secrete proteases.

In an aspect, the chemistry for crosslinking between microparticles may be different than the chemistry for crosslinking the bulk of the microparticles as described herein above. In various aspects, the hydrogel microparticles are cross-linked together in the absence of living cells or in the presence of living cells. In another aspect, cells may be seeded in or on the formed scaffold. Cells may migrate into and through the scaffold for tissue engineering or regenerative medicine purposes. In one aspect, the cells are surrounded by the microparticles but are not encapsulated in the microparticles. The thickness and shape of the scaffold can vary depending upon the intended use of the scaffold.

A time for microparticle formation may be chosen so that microparticles exist primarily as isolated particles or aggregates of less than about 10 microparticles. Then, different types of microparticles may be mixed and used to form a scaffold, imparting properties of each of the types of microparticles on the scaffold as a whole. The microparticles may also be linked together in a scaffold in a way that introduces a gradient in some property, which may be advantageous in directing cell, tissue or blood vessel responses to the material. Thus, a highly modular approach to scaffold formation is possible.

Functional agents, such as proteins and peptides may also be added to the scaffolds, which may impart biological activity but not necessarily enhance scaffold formation. Proteins and peptides that enhance scaffold formation may also be chosen to impart biological activity in the scaffolds. Examples include cell adhesion peptides, growth factors, and antibodies, particularly antibodies directed against stem cells or progenitor cells. By incorporating glutathione into the microparticles, the scaffolds may also trap proteins containing a GST tag, including enzymes that produce bioactive lipids such as a sphingosine kinase-GST fusion protein, or chondroitinase ABC. By incorporating heparin and GDNF, the scaffold may encourage neurite extension through the scaffold. By incorporating laminin, the scaffold may encourage cell adhesion and migration. By incorporating heparin without GDNF or any other exogenous growth factor, endogenous growth factors may also be bound and slowly released from the scaffolds.

Microparticles formed by the process of the present disclosure may also be mixed with microparticles made by known processes prior to scaffold formation. For example, poly(lactic/glycolic) acid microparticles containing growth factors may be incorporated in the scaffold.

Scaffold formation is modular with regard to the different types of microparticles that may be mixed to form the scaffolds. The mixture of microparticles does not need to be homogenous and, consequently, scaffolds comprising gradients of different microparticles may be formed. Gradients may be introduced using differences in microparticle density, which can be accomplished by incubating microparticles for different lengths of time in the phase-separated state. For example, a gradient may be formed in one step, using density (buoyancy) differences in microparticles to form distinct layers during centrifugation. Gradients may also be introduced by modifying the net charge on different microparticles and using electrophoresis to separate the microparticles. Gradients may also be introduced using a gradient mixer containing different types of microparticles in the different reservoirs of the gradient mixer. Gradients may be formed by other means, for example, by gently layering solutions containing microparticles with different properties on top of each other.

The rate of cell migration through the scaffold may be improved by having a gradient of enzymatic degradability between microparticles in the scaffold. If the degradability between microparticles is greater than within the microparticle, cells may degrade between microparticles before degrading the bulk of the microparticles, creating pathways for cell migration between the microparticles. Alternatively, greater degradability within the microparticles may allow the creation of large voids but leaving a network between the microparticles that may provide mechanical support.

Microparticles with varying rates of plasmin degradability as described herein above may be layered to form a scaffold with varying degradability over longer distances (>100 microsphere diameters). In an aspect, the incubation time of the degradable microparticles in the phase separated state at 70° C. may determine the extent of degradability. In various aspects, the incubation time may range from about 8 min to about 10 min for multiarm clickable PEG crosslinked scaffolds, where the longer the time of incubation the longer it may take for plasmin to degrade the crosslinks. If linear clickable PEG is used to crosslink microparticles to form a scaffold, the upper limit may be increased from 10 min to about 45 min, at which point microparticle aggregation may become too great. The scaffold may include a gradient of enzymatic degradability along the length of the scaffold to encourage guided cell growth and migration through the scaffold.

In one aspect, the gradient may encourage cell growth and migration from the proximal end of the scaffold to the distal end of the scaffold by having the crosslinks between microparticles at the proximal end degrade faster than the crosslinks between microparticles at the distal end of the scaffold. The scaffold may include at least two layers of microparticles with different plasmin degradability to form the gradient of degradability within the scaffold. The gradient may become more linear with the addition of more layers of microparticles to the scaffold. In various aspects, the scaffold may include at least 2 layers, at least 3 layers, at least 4 layers, at least 5 layers, at least 6 layers, at least 7 layers, at least 8 layers, at least 9 layers, or at least 10 layers. In one aspect, the scaffold with the gradient of degradability may be held within a nerve guidance conduit to encourage neuron growth through the scaffold and nerve guidance conduit for peripheral nerve regeneration.

The bulk and/or the surface of the microparticles may include a functional agent such as cell adhesion molecules, growth factors, and/or growth factor binding molecules to enhance the migration of the cells between the microparticles. In an aspect, the microparticles in the scaffold may include cell adhesion molecules, which may further allow the cells to migrate between the microparticles and deposit extracellular matrix (ECM). After degradation between the microparticles, the bulk of the microparticles may dissolve, allowing for the eventual replacement of the scaffold with tissue.

In an aspect, scaffolds with a concentration gradient of a functional agent may be formed by sequentially centrifuging microparticles in distinct layers, with gradients of a functional agent formed by incubating microparticles with different concentrations of a desired protein or peptide prior to and/or during centrifugation. In one aspect, the desired protein may be glial-cell derived human neurotrophic factor (GDNF). The layer-by-layer scaffold formation method may eliminate the high sensitivity of the microparticle structure to the length of incubation time in the phase separated state during microparticle formation. Although the layer-by-layer method initially produces step gradients in GDNF, continuous gradients of soluble GDNF are rapidly generated by diffusion and dynamic interactions with heparin in the scaffold. In various aspects, the scaffold may include between about 1 and about 20 layers of microparticles to create a gradient along the scaffold.

Figure 11A:
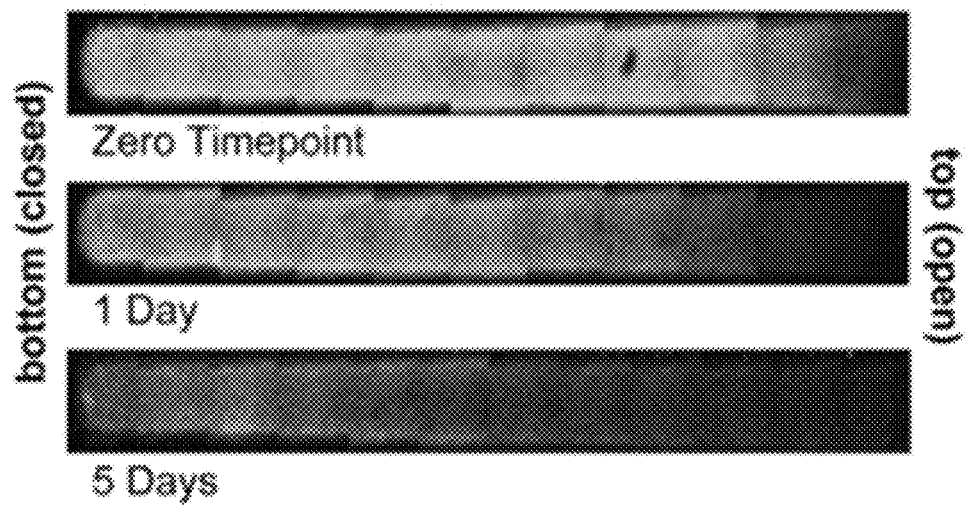
FIG. 11A is a composite photograph of physiological salt (PBS) release of Dylight-488 labeled GDNF (constant initial profile) from a Heparin decorated PEG microparticle (11 min incubation) scaffold at the zero time point, one day, and 5 days.
Figure 11B:
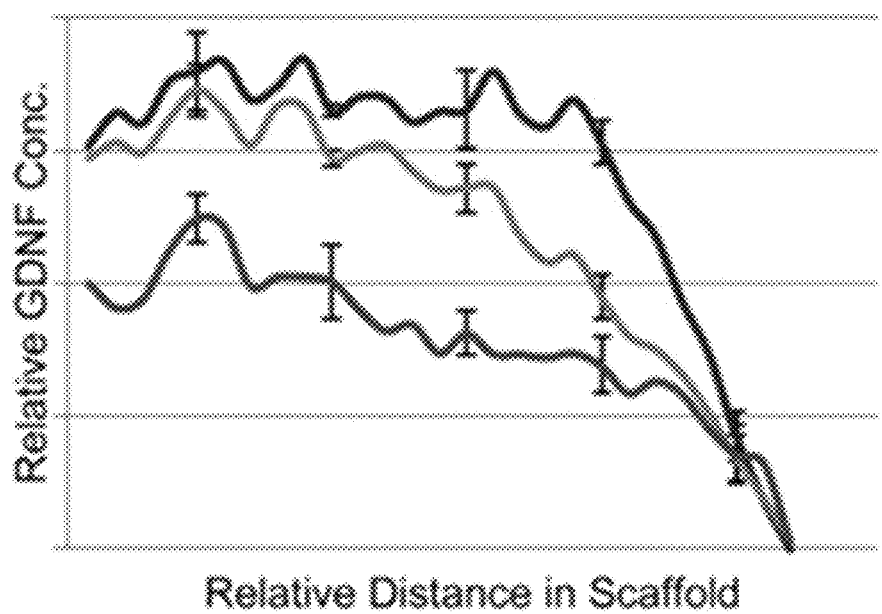
FIG. 11B is a graphical depiction of fluorescence (GDNF concentration) vs. the distance in the scaffold for the three time points: zero (blue), 1 day (green), and 5 days (red). n=3 sample, error bars shown.
Figure 11C:
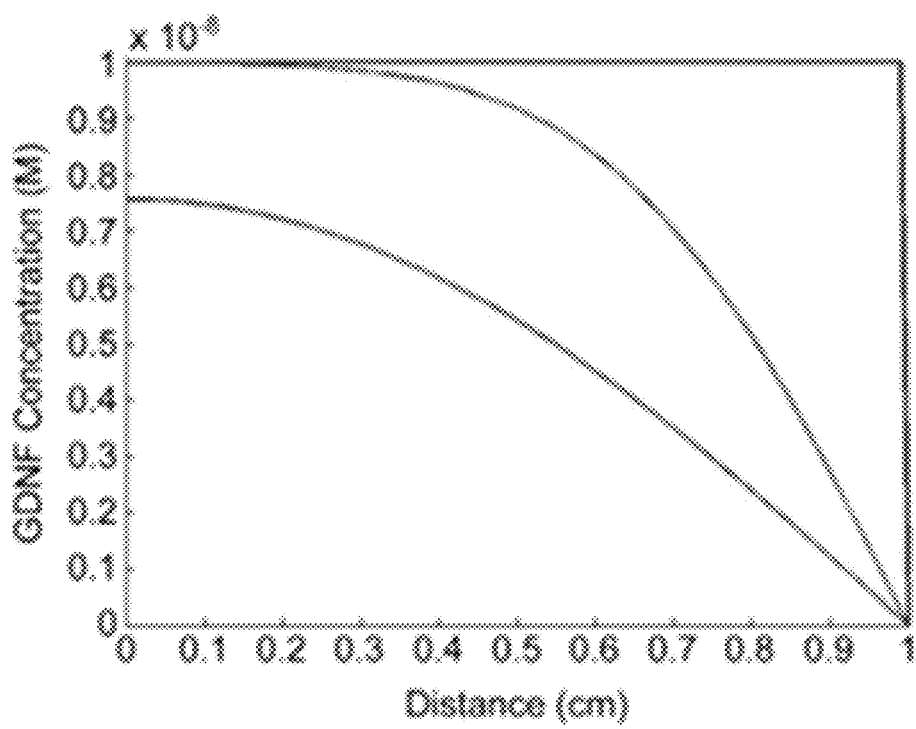
FIG. 11C is a plot of predicted release (GDNF Concentration vs. distance in the scaffold) based on Fick's 2nd law. Zero time point (blue), 1 day (green), and 5 days (red).
Figure 12A:
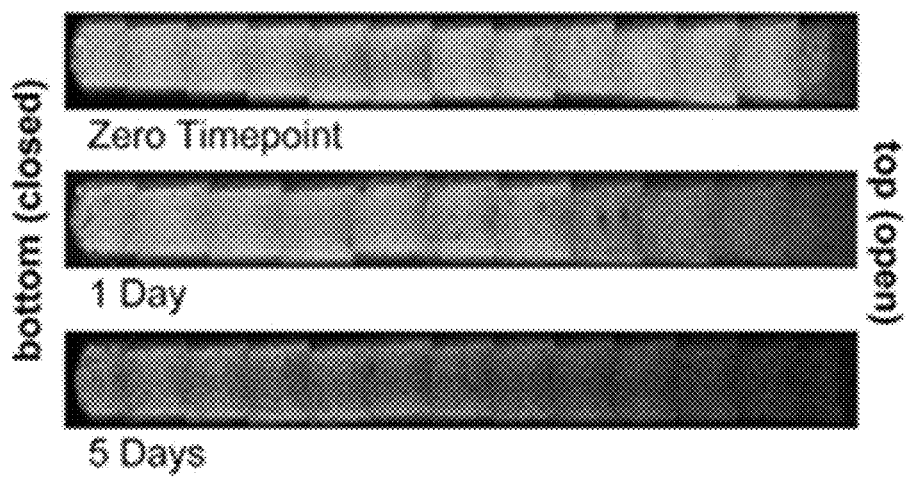
FIG. 12A shows "Low salt" (8 mM Sodium phosphate) release of Dylight-488 labeled GDNF (constant initial profile) from Heparin decorated PEG microparticle (11 min incubation) scaffold. Composite photograph of fluorescence (GDNF) in scaffold at the zero time point, one day, and 5 days.
Figure 12B:
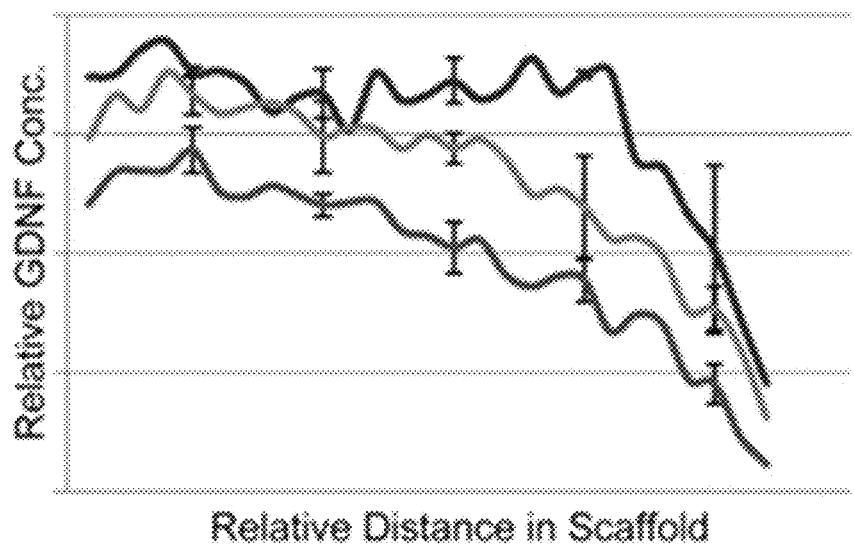
FIG. 12B is a graphical depiction of fluorescence (GDNF concentration) vs. the distance in the scaffold for the three time points: zero (blue), 1 day (green), and 5 days (red). n=3 sample, error bars shown.
Figure 12C:
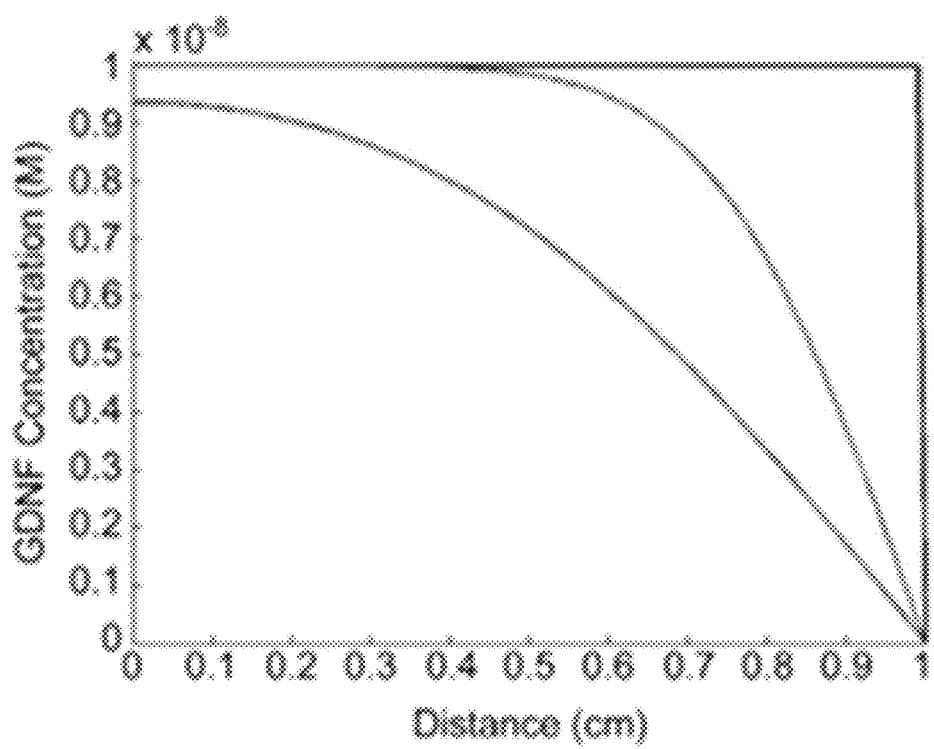
FIG. 12C is a plot of predicted release (GDNF Concentration vs. distance in the scaffold) based on Fick's 2nd law. Zero time point (blue), 1 day (green), and 5 days (red).
Figure 13A:
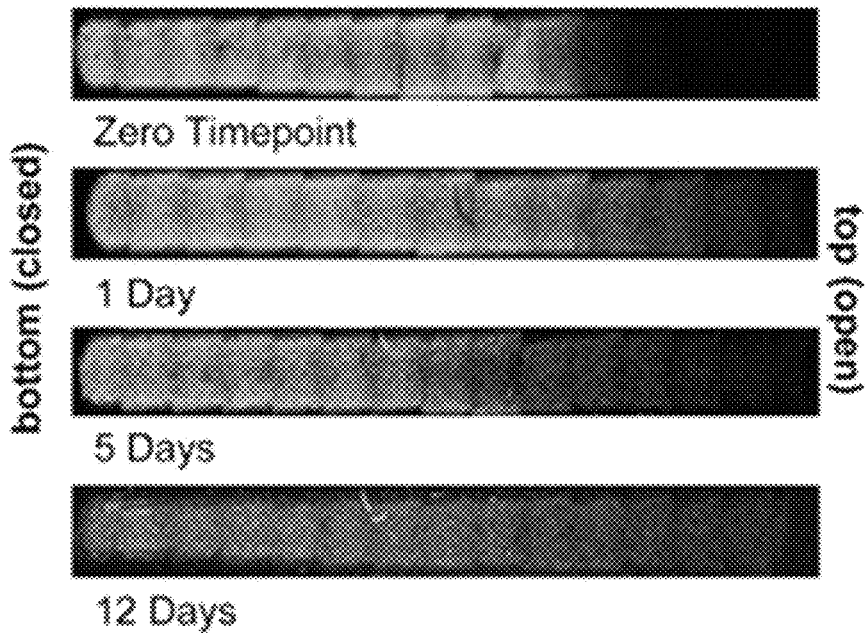
FIG. 13A shows a 2-tier initial profile, physiological salt (PBS) release of Dylight-488 labeled GDNF from Heparin decorated PEG microparticle (11 min incubation) scaffold. Composite photograph of fluorescence (GDNF) in scaffold at the zero time point, one day, 5 days, and 12 days.
Figure 13B:
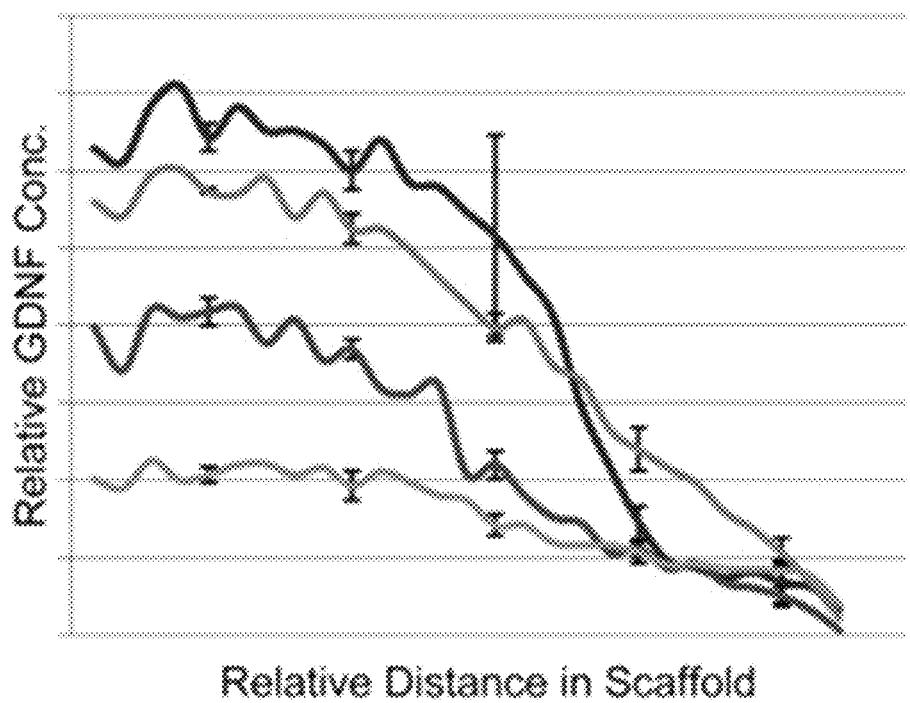
FIG. 13B is a graphical depiction of fluorescence (GDNF concentration) vs. the distance in the scaffold for the four time points: zero (blue), 1 day (green), 5 days (red), and 12 days (light blue). n=3 sample, error bars shown.
Figure 13C:
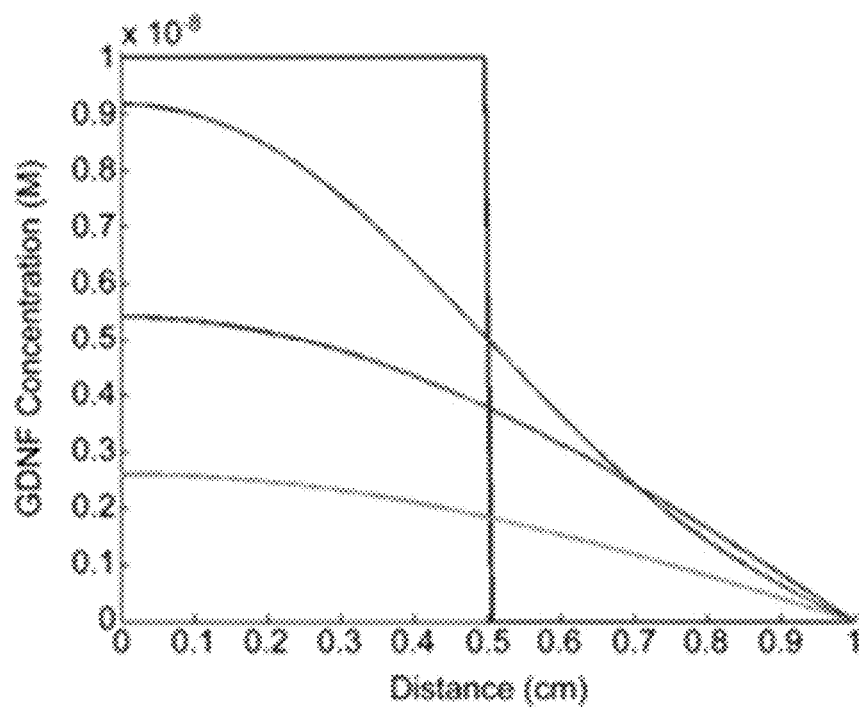
FIG. 13C is a plot of predicted release (GDNF Concentration vs. distance in the scaffold) based on Fick's 2nd law. Zero time point (blue), 1 day (green), 5 days (red), and 12 days (light blue).
Figure 14A:
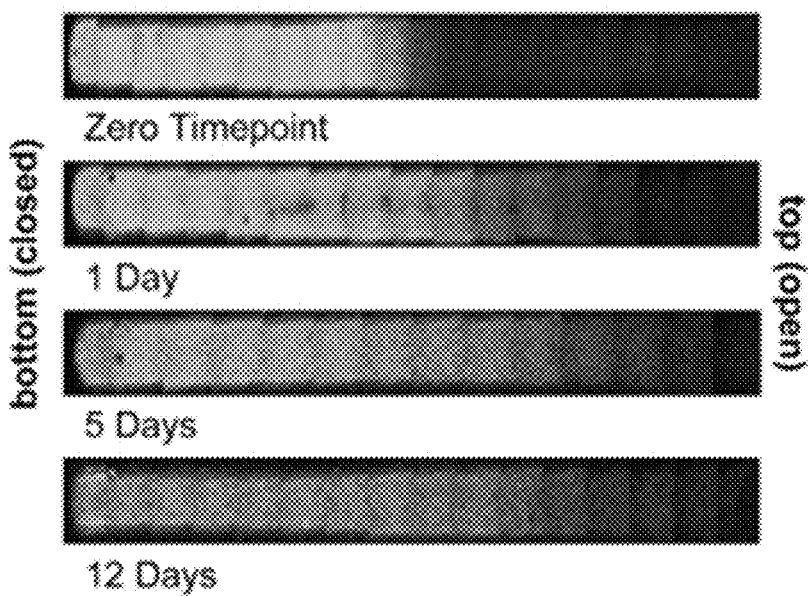
FIG. 14A shows a 2-tier initial profile, "low salt" (8 mM sodium phosphate) release of Dylight-488 labeled GDNF from Heparin decorated PEG microparticle (11 min incubation) scaffold. Composite photograph of fluorescence (GDNF) in scaffold at the zero time point, one day, 5 days, and 12 days.
Figure 14B:
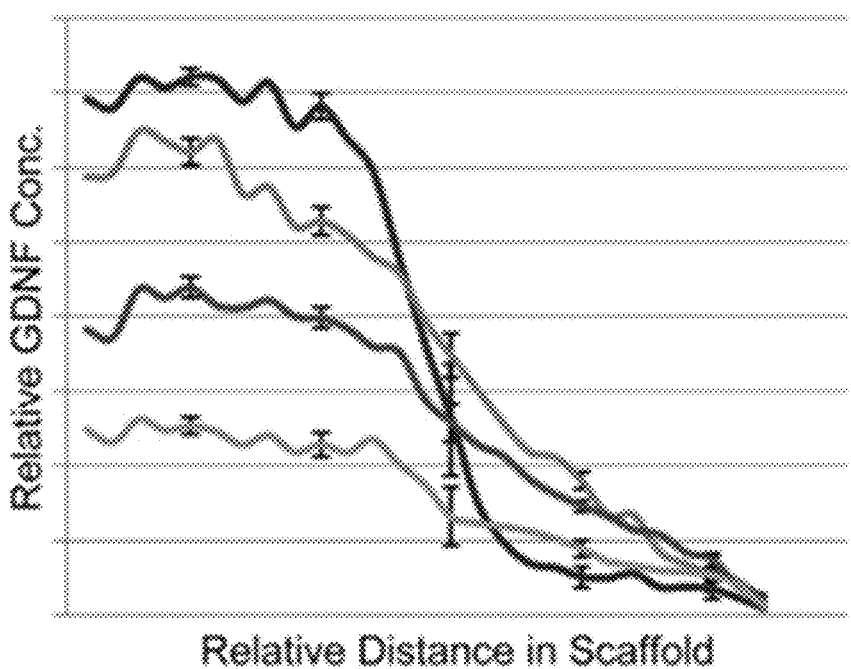
FIG. 14B is a graphical depiction of fluorescence (GDNF concentration) vs. the distance in the scaffold for the four time points: zero (blue), 1 day (green), 5 days (red), and 12 days (light blue). n=3 sample, error bars shown.
Figure 14C:
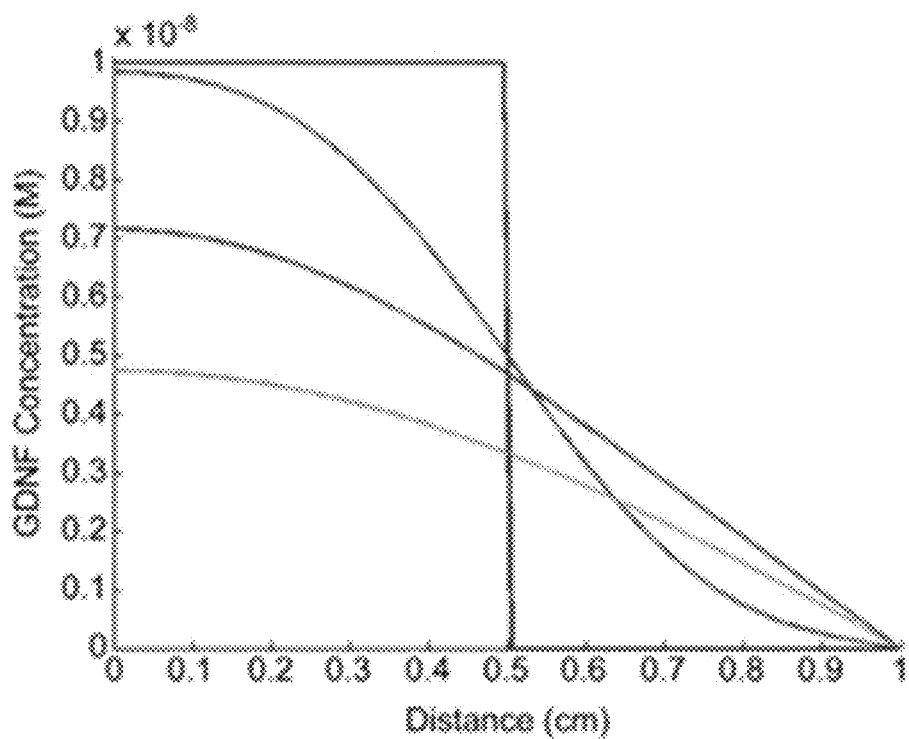
FIG. 14C is a plot of predicted release (GDNF Concentration vs. distance in the scaffold) based on Fick's 2nd law. Zero time point (blue), 1 day (green), 5 days (red), and 12 days (light blue).

FIGS. 11 and 12 show release for single tiered scaffolds made of heparin-containing microparticles incubated in 250 ng/mL GDNF during scaffold formation. FIGS. 13 and 14 show scaffolds with two tiers—a lower tier with scaffold made of heparin-containing microparticles incubated in 250 nM GDNF during centrifugation, and an upper level with no GDNF present during centrifugation of heparin containing microparticles. FIGS. 11A, 12A, 13A, and 14A demonstrate gradient formation within one or two tier scaffolds, with release into either physiological (FIGS. 11 and 13) and low salt conditions (FIGS. 12 and 14). The affinity of GDNF for heparin in the microparticles may be influenced by the concentration of salt in the surrounding buffer. Low salt (about 8 mM sodium phosphate) may result in slower release than physiological salt concentrations (i.e. PBS).

GDNF may be more rapidly released into buffer at physiological salt concentration, as seen in FIGS. 11B, 12B, 13B and 14B.

Each of these figures also contains mathematical predictions for the GDNF concentration profile within the scaffold based on Fick's 2nd Law (FIGS. 11C, 12C, 13C and 14C). The prediction was obtained using a model that utilized an effective diffusion constant for GDNF within the scaffold:

$$D_{eff} = \frac{D_{AB}}{[H]/K_D + 1}$$

where $D_{eff}$=effective diffusion constant, DAB=diffusion constant of GDNF in PEG scaffolds without heparin, [H]=heparin concentration, KD=equilibrium dissociation constant for the interaction of heparin with GDNF. Use of an effective diffusion coefficient is justified when binding equilibrium is rapidly achieved compared to the rate of diffusion. The release data in FIGS. 11-14 were fit to solutions of Fick's second law to determine best fit effective diffusion coefficients. In physiological salt a $D_{eff}$=4.84×10$^{-8}$ cm$^2$ s$^{-1}$ was observed, while in low salt a $D_{eff}$=2.52×10$^{-8}$ cm$^2$ s$^{-1}$ was observed. The differences may be explained by the higher affinity of GDNF for heparin in low salt conditions. All predicted curves in FIGS. 11-14 used these values for the effective diffusion coefficients.

Figure 15A:
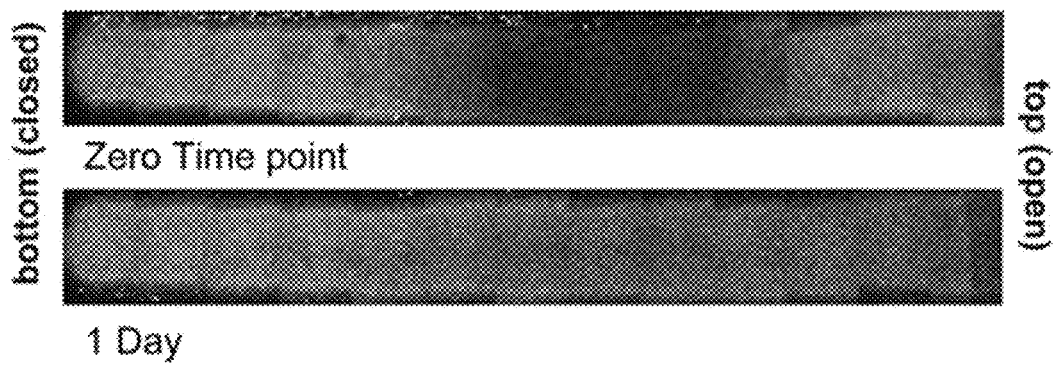
FIG. 15A shows a 3-tier initial pattern: GDNF-Empty-GDNF. The versatility of this gradient formation technique is displayed by three scaffolds with more complex patterns of GDNF. Composite photographs of fluorescence (GDNF) in the scaffolds taken at the zero time point and after one day.
Figure 15B:
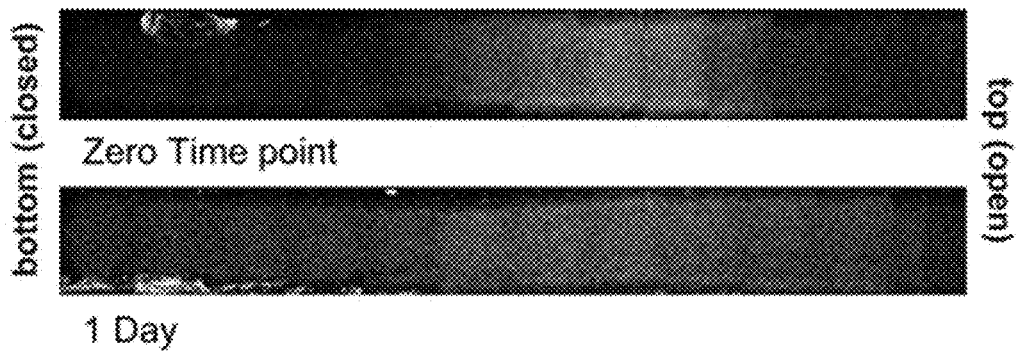
FIG. 15B shows a 3-tier initial pattern: Empty-GDNF-Empty.
Figure 15C:
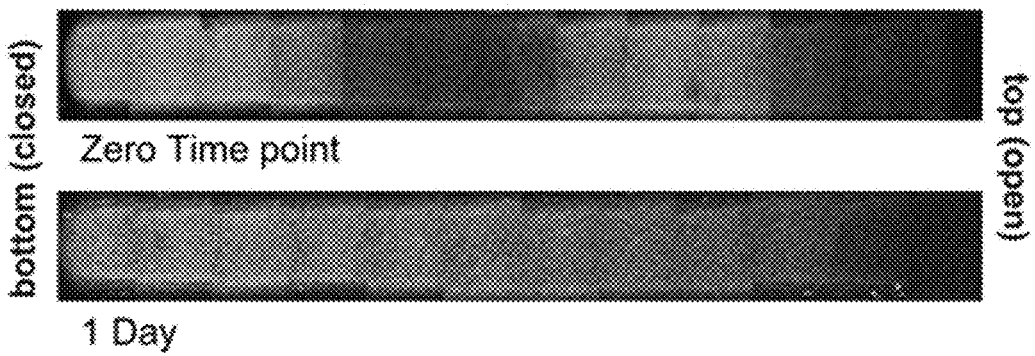
FIG. 15C shows a 4-tier initial pattern: GDNF-Empty-GDNF-Empty.

The presence of a linear gradient in protein or peptide concentration may emerge in a layered scaffold in about one day and may be maintained for about 12 days to about 90 days. In various aspects, more complex layer-by-layer arrangements may allow for the engineering of not only release kinetics but also gradient shape. Multiple tiered scaffolds may be fabricated with different amounts of protein or peptide in the tiers. FIG. 15 shows three and four-tiered scaffolds with GDNF initially in alternating tiers. These examples display the ability of this method to create more complex concentration profiles and release kinetics. The multiple tiers could also be incubated with distinct concentrations of different growth factors, allowing release of multiple growth factors with different concentration profiles and release kinetics. The heparin content in the different tiers may also be varied to affect the release kinetics and gradient-forming capabilities of the scaffolds.

In some embodiments, the scaffold may provide a generic three-dimensional tissue culture system. Scaffolds may be formed and then seeded with cells or implanted for cell ingrowth. Scaffolds may be formed from a variety of particles to introduce macropores or biological functionalities that encourage cell in-growth and/or angiogenesis. These properties may be present in the form of gradients of microparticle types and/or a gradient of degradation between the microparticles. In some aspects, cells may be mixed with the microparticles prior to cross-linking. In other aspects, native cells may migrate into the scaffold. Non-limiting examples of exemplary cells include fibroblasts, epithelial cells, blood cells, precursor blood cells, immune system cells, hepatocytes, renal cells, chondrocytes, osteoblasts, respiratory tract cells, gut cells, bladder cells, pancreatic cells, myoblasts, skeletal muscle cells, heart muscle cells, smooth muscle cells, exocrine gland cells, hormone secreting cells, sensory transducer cells, neurons, neuron supporting cells, and stem cells. If the scaffolds rapidly promote the in-growth of blood vessels due to delivery of angiogenic agents, cell survival may enhance the formation of functional tissues. Rapid ingrowth of nerves may enhance physiological control of the new tissue.

In a general preferred embodiment, microparticles are formed from a biocompatible hydrogel material that is enzymatically degradable using any chemistry and processing method available. The surface or bulk of the microparticles is engineered to contain a click group that does not react to a measurable extent with thiols or amines in water at pH 7.4 at 37° C. over 24 hours. A second batch of microparticles is also produced, identical to the first except containing a click group that reacts with the first set of microparticles. By placing the microparticles together, a scaffold is formed over a period of time, which may be shortened by centrifuging or phase separating the polymer in the microparticles with sodium sulfate, dextran, etc. The rate of degradation of the bulk of the microparticles is determined by the crosslink density of the material, with a greater number of crosslinks requiring more enzymatic cleavage reactions to liquefy the microparticles. In contrast, the degradability between the microparticles depends on both the density of intraparticle crosslinks at the surface of the microparticle, which may be different than within the bulk, and the density of interparticle crosslinks, which depends upon the efficiency of the reaction between click groups in adjacent microparticles. The interparticle degradability may be further tuned by using an enzyme-sensitive peptide sequence as a part of the polymer containing the click group. This enzyme-sensitive peptide may be the same or different from that used in the bulk of the microparticle. It is understood that an enzyme-sensitive peptide could be readily replaced with any enzyme-sensitive chemical that is not a peptide.

Figure 17A:
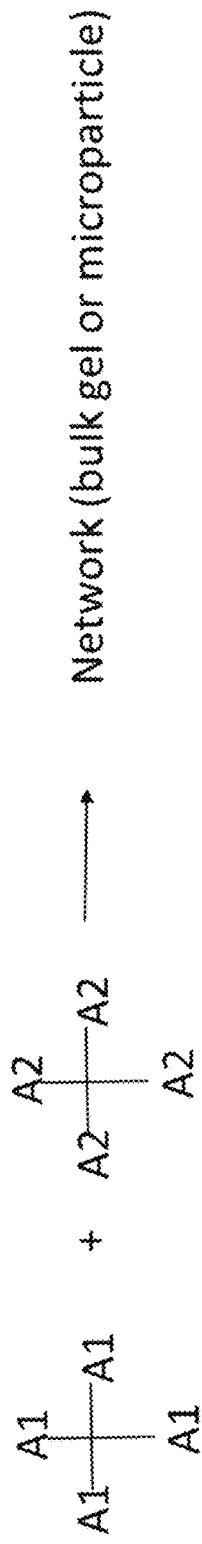
FIG. 17A is an illustration of microparticles formed via a reaction 'A'.
Figure 17B:
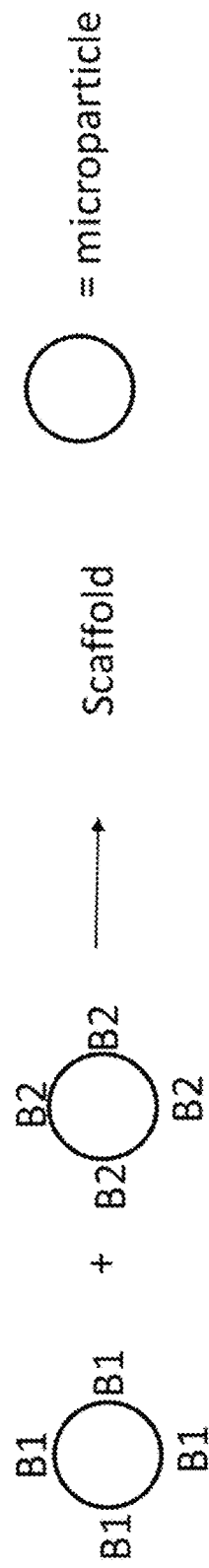
FIG. 17B is an illustration of a scaffold formed via a reaction 'B'. Reaction 'A' is orthogonal to the reaction 'B' that is used to crosslink the microparticles.

In general, as illustrated by FIG. 17, microparticles may be formed via a reaction 'A' that is orthogonal to a reaction 'B' that is used to crosslink microparticles. The advantage of this strategy is that the microparticles may be synthesized using the 'A' chemistry, then one or more of the constituents of the 'A' chemistry may be quenched, and microparticles may be characterized while in a state that cannot lead to microparticle aggregation. Furthermore, if reaction 'B' is a click chemistry, biological molecules may be present in the materials for extended periods of time without risk of damage by reaction with chemical groups in the material.

Quenching of 'A' groups may lead to enhanced 'shelf life' of the scaffolds, allowing them to be stored for periods of months or years before use. If 'A' groups were not quenched, groups such as amines and thiols on biological molecules may react with 'A' groups in the material over time. Sensitive biological agents such as growth factors may be safely added to the microparticles after quenching.

The 'A' reaction may also be a click chemistry, although it is necessary that the 'A' click chemistry and the 'B' click chemistry be orthogonal. Once formed using the 'A' click chemistry, the microparticles may be split into two batches and each may receive one constituent of the 'B' click chemistry.

Microparticles may be made via 'A' chemistry (click or not) with one constituent of the 'B' click chemistry already present, assuming that the constituent of the 'B' click chemistry does not interfere with the 'A' chemistry.

A constituent of the 'A' chemistry may be reused in the 'B' chemistry assuming that the other constituent of the 'A' chemistry may be quenched. For example, microparticles may be formed using reaction of a thiol with a vinylsulfone. After quenching the residual vinylsulfone in the microparticle with a second thiol-containing molecule, the residual thiol groups can be activated with free-radicals to participate in a thiol-ene or thiol-yne reaction to form a scaffold.

A desirable property of the 'A' chemistry is the ability to add biological molecules via reaction through their amines and/or thiols. This reduces the usefulness of a click chemistry in the 'A' chemistry. However, one of the constituents of the 'A' click reaction may be synthesized as a bifunctional molecule, combining a click group with a chemical group that has reactivity towards amines or thiols. This linker molecule is reacted with the biological molecule and the product may be included during microsphere formation or following microsphere formation. Similarly, a bifunctional molecule may also be used to couple biological molecules to the formed microparticles via the 'B' chemistry.

A preferred 'A' chemistry is vinylsulfone reacted with an amine and a preferred 'B' chemistry is a strained alkyne reacted with azide groups.

EXAMPLES

The following examples illustrate various embodiments of the present disclosure.

Example 1: PEG Synthesis $PEG_8$-vinyl sulfone ($PEG_8$-VS) and $PEG_8$-amine were synthesized from eight-arm PEG-OH ($PEG_8$-OH; mol. Wt. 10,000; Shearwater Polymers, Huntsville, Ala.) as previously described [56]. PEG macromonomers were dissolved separately at 200 mg/mL in Dulbecco's phosphate buffered saline (PBS; 8 mM sodium phosphate, 2 mM potassium phosphate, 140 mM sodium chloride, 10 mM potassium chloride, pH 7.4) and sterile filtered with 0.22 mm syringe filters (Millipore).

Example 2: Heparin Attachment Pre-Microparticle Formation (For High Heparin Microparticles)

A solution of 244 mg/mL Heparin sodium salt (mol. wt. ~18,000, ~2.78 mM), 0.081 mM N-(3-Dimethylaminopropyl)-NO-ethylcarbodiimide hydrochloride (EDC), and 0.203 mM N-Hydroxysuccinimide (NHS) in MES buffer (10 mM, pH 6.0) was incubated at room temperature for 30 min. L-Cysteine (free base) was added to the activated heparin solution to make a 6:1 cysteine:heparin molar ratio and allowed to react overnight. The solution was dialyzed in 10×PBS (pH 7.4) to remove unreacted cysteine. Ellman's assays were performed to determine substitution of cysteine on heparin (44% of heparin molecules determined to have cysteine). $PEG_8$-VS was added at a 10:3 $PEG_8$-VS:cysteinated-heparin molar ratio and incubated at room temperature overnight. For microparticle formation, heparin-conjugated $PEG_8$-VS was mixed with $PEG_8$-amine in a 1:1 ratio of the two PEG types.

Example 3: Ellman's Assay

Ellman's reagent was dissolved in 0.1 M phosphate buffer (pH 8.0) at 40 mg/mL 0.05-0.15 μmol of cysteinated heparinwas added to 3 mL of 0.1 M phosphate buffer (pH 8.0) along with 100 mL Ellman's solution. The solution was mixed and incubated at room temperature for 15 min. Absorbance at 412 nm was measured and compared to standard to determine cysteine content.

Example 4: High Heparin Microparticle Formation

Heparinated $PEG_8$-VS solutions were combined with $PEG_8$-amine solutions at a 1:1 ratio. The PEG solutions were diluted to 20 mg/mL PEG with PBS and 1.5 M sodium sulfate (in PBS) to a final sodium sulfate concentration of 0.6 M. The $PEG_8$-VS/$PEG_8$-amine solutions were then incubated above the cloud point at 70° C. for 11 min. Suspensions of microparticles were subsequently buffer exchanged into 8 mM sodium phosphate twice to remove the sodium sulfate by: (1) diluting the microparticle solution 3:1 with PBS and titurating, (2) centrifuging at 14,100 g for 2 min, and (3) removing the supernatant. Fluorescent and phase contrast images were captured using a MICROfire (Olympus, Center Valley, Pa.) camera attached to an Olympus IX70 inverted microscope.

Example 5: Heparin Attachment Post-Microparticle Formation

A solution of 515 mg/mL Heparin sodium salt (mol. wt. ~18,000, ~2.78 mM), 0.101 mM N-(3-Dimethylaminopropyl)-N'-ethylcarbodiimide hydrochloride (EDC), and 0.042 mM N-Hydroxysuccinimide (NHS) in MES buffer (10 mM, pH 6.0) was incubated at room temperature for 30 min. L-Cysteine (free base) was added to the activated heparin solution to make a 8.82:1 cysteine:heparin molar ratio and allowed to react overnight (see FIG. 1A). The solution was dialyzed in 10×PBS (pH 7.4) to remove unreacted cysteine. Ellman's assays were performed to determine substitution of cysteine on heparin (109% of heparin molecules determined to have cysteine). The solution was diluted to 130 mg/ml heparin and stored at −20° C. For heparination of microparticles, cysteine conjugated heparin was added to PEG microparticles at 2.6 mg/mL and incubated overnight.

Example 6: Heparin Labeling

To confirm post-microparticle formation attachment, cysteinated heparin was labeled with Dylight-488 NHS-ester (Pierce). Cysteinated heparin (130 mg/mL) and Dylight-488 (560 mg/mL) in PBS was incubated overnight at room temperature. The labeled heparin solution was dialyzed using Slide-A-Lyzer MINI Dialysis Units (Thermo Scientific, Rockford, Ill., 3500 MWCO) in PBS (pH 7.4) to remove any unbound Dylight-488. The heparin solution was then used in the heparination post-microparticle formation protocol as described above. To determine heparin content, fluorescence of the suspended microparticle solution was measured using a plate reader in triplicate and compared to a standard curve of fluorescently labeled heparin in solution.

Example 7: Plasmin-Degradable PEG Synthesis

Peptide sequence Ac-GCGGVRNGGK—$NH_2$ (N-Terminal Acetylation, C-Terminal Amidation, Purity >95%, GenScript USA Inc., Piscataway, N.J.) was dissolved in 0.1 M phosphate buffer at 117.9 mg/mL with $PEG_8$-VS (200 mg/mL, 78% substitution) and brought to a pH of 7.4. The solution was incubated overnight at room temperature before storage at 4° C.

Example 8: Plasmin-Degradable Microparticle Formation $PEG_8$-VS solutions were combined with plasmin degradable $PEG_8$-VS (PEG-$(VRN)_8$) solutions at a 1:1 molar ratio and incubated at 37° C. for 1 h. The PEG solutions were diluted to 20 mg/mL PEG with PBS and 1.5 M sodium sulfate (in PBS) to a final sodium sulfate concentration of 0.6 M. $PEG_8$-Azide/Amine or $PEG_8$-Cyclooctyne/Amine were added to the PEG solution at a 50:1 PEG$_8$-VS/PEG-(VRN)$_8$ to Clickable PEG ratio. The PEG solution was then incubated above the cloud point at 70° C. for various times. Suspensions of microparticles were subsequently buffer exchanged into 8 mM sodium phosphate buffer twice to remove the sodium sulfate by: (1) diluting the microparticle solution 3:1 with PBS and titurating, (2) centrifuging at 14,100 g for 2 min, and (3) removing the supernatant (see FIG. 1B).

Example 9: PEG$_8$-Azide/Amine Synthesis

Eight arm PEG-mesylate (PEG$_8$-mesylate; mol wt 10,000) was first synthesized from four arm PEG-OH (PEG$_8$-OH; mol wt 10,000; Creative PEGWorks) by mesylating the alcohol group on PEG$_8$-OH with mesyl chloride. This was done by dissolving PEG$_8$-OH in dichloromethane (DCM), adding four equivalents of triethylamine and four equivalents of methanesulfonyl chloride while on ice, and letting it react overnight under constant stirring and nitrogen flow. After removing the salt byproduct, excess DCM was removed by using a rotovap, and the PEG$_8$-mesylate was precipitated using cold diethyl ether. The product was dried under vacuum overnight to remove remaining diethyl ether. The next step was the nucleophilic azidation of the mesylate group with sodium azide. Three equivalents of sodium azide were dissolved in dimethyl formamide (DMF). PEG$_8$-mesylate was then dissolved in the DMF mixture and put under nitrogen and constant stirring in a hot water bath at 60° C. The reaction was run overnight. The following day required the filtration of excess salt followed by rotovapping, diethyl ether precipitation, and drying as was done for the PEG$_8$-mesylate. The product was dissolved in a basic water solution with a pH between 9 and 12, and then extracted with DCM over anhydrous sodium sulfate (Na$_2$SO$_4$). A standard extraction procedure was done to extract the product into DCM. After three extractions, the Na$_2$SO$_4$ was filtered out and the process of rotovapping, diethyl ether precipitation, and drying was repeated as before. 1H NMR (300 MHz, CDCl$_3$, δ): (s, 902.55H, PEG), 3.0 (s, 3H, —SO$_2$CH$_3$), 4.3 (t, 2H, —CH$_2$OSO$_2$—). NMR of the product confirmed that no mesylate features remained at 3.0 ppm and 4.3 ppm.

PEG$_8$-azide was dissolved in tetrahydrofuran (THF) and 1.15 equivalents of triphenylphosphine (TPP) and 30 equivalents of ultrapure H$_2$O were added while on ice, and the reaction was allowed to go overnight under constant stirring and nitrogen flow. A large excess of H$_2$O to TPP was needed for amine formation. Excess THF and H$_2$O were removed by rotovapping, and PEG$_8$-Azide/Amine and triphenylphosphine oxide (TPPO) were precipitated out using cold diethyl ether. The product and byproduct were dried under vacuum overnight to remove remaining diethyl ether. Once dry, the PEG$_8$-Azide/Amine and TPPO were added to cold toluene, because TPPO is soluble in cold toluene while PEG is insoluble. The PEG$_8$-Azide/Amine was then vacuum filtered to remove the TPPO. The product then underwent the same extraction procedure with DCM that was described for PEG$_8$-Azide synthesis. 1H NMR (300 MHz, CDCl$_3$, d):(s, 902.55H, PEG), 2.9 (t, 2H, —CH$_2$CH$_2$NH$_2$). NMR of the product confirmed the reduction of about 50% of azides to amines via the amine feature at 2.9 ppm.

Example 10: PEG$_8$-Cyclooctyne/Amine Synthesis

Amines on PEG$_8$-Amine (prepared as previously described) were partially reacted with a cyclooctyne-containing molecule to form PEG$_8$-Cyclooctyne/Amine.

PEG$_8$-Amine was dissolved in DCM, and 0.5 equivalents of diisopropylcarbodiimide (DIPCDI) were added to a separate flask with DCM while on ice and under nitrogen flow and constant stirring. Next, 0.5 equivalents of hydroxybenzotriazole (HOBt) and 0.5 equivalents of aza-dibenzocyclooctyne with a pendant carboxylic acid (DBCO-acid; Click Chemistry Tools) were added to the mixture and allowed to stir for 10 min. While waiting, one equivalent of N,N-diisopropylethylamine (DIPEA) was added to the dissolved PEG$_8$-Amine. Finally, this mixture was slowly added to the activated DBCO, and the reaction was allowed to proceed for 24 h on an ice bath under constant stirring and nitrogen gas. Following that process, the urea precipitate was filtered out, and rotovapping, diethyl ether precipitation, and drying were performed. The product was then dissolved in distilled H$_2$O and underwent the same extraction procedure that was done for the PEG$_8$-Amine. Further rotovapping, diethyl ether precipitation, and drying were done. 1H NMR (300 MHz, CDCl$_3$, δ): (s, 902.55H, PEG), 5.1 (d, 2H, —CH$_2$—). NMR of the product confirmed the conversion of 50% of amines to cyclooctynes (PEG$_8$-Cyclooctyne/Amine) via the presence of a doublet at 5.1 ppm.

Example 11: Clickable Microparticle Formation

PEG$_8$-Azide/Amine and PEG$_8$-Cyclooctyne/Amine were separately dissolved in 0.1 M phosphate buffer (pH 7.4) at 40 mg/mL. Dylight-633 NHS-ester (Pierce) was dissolved in dimethyl formamide at 10 mg/mL and added to the clickable PEG's such that final concentrations were 33.33 mg/mL clickable PEG and 1.67 mg/mL Dylight. Solutions were incubated overnight at 25° C. to allow near complete reaction. The same methods for degradable microparticle formation were followed, except that just prior to dilution in 0.6 M sodium sulfate, PEG$_8$-Azide/Amine and PEG$_8$-Cyclooctyne/Amine were added to separate batches of the degradable microparticle precursor solution at a 1:50 molar ratio of clickable PEG to all other PEG. The methods for degradable microparticle formation given above were followed from this point, keeping the batches containing PEG$_8$-Azide/Amine or PEG$_8$-Cyclooctyne/Amine separate until just prior to scaffold formation (see FIG. 1C).

Example 12: Laminin Attachment

Laminin Mouse Protein, Natural (Life Technologies, Grand Island, N.Y.) was added to microparticles at 20 mg/mL or 2-D gel at 0.8 mg/mL and incubated at 37° C. overnight.

Example 13: Cysteine Capping of Vinyl-Sulfones

After all other functionalities were added to the microparticles (the last step being incubation with thiolated heparin and laminin), the microparticles were washed 2× and re-suspended in 2.5 mg/mL L-cysteine and incubated for 30 min at room temperature. The microparticles were then washed 3× before use.

Example 14: GDNF Loading of Microparticles

Recombinant human GDNF (Peprotech, Rocky Hill, N.J.) was dissolved in 8 mM sodium phosphate buffer (pH 7.4) and added to washed microparticles such that the GDNF concentration within the supernatant was 250 ng/mL (note higher concentrations used for DRG experiments below). The microparticle/GDNF solution was well mixed by tituration and incubated 2 h at 4° C. to allow diffusion of GDNF into the microparticles. Immediately before scaffold formation, the microparticles were centrifuged at 14,100 g, supernatant was removed, and microparticles were re-suspended in 8 mM sodium phosphate.

Example 15: GDNF Labeling

Dylight-488 NHS-ester (Pierce) was dissolved in dimethyl formamide at 10 mg/mL. Recombinant human GDNF (Peprotech, Rocky Hill, N.J.) was dissolved in 8 mM sodium phosphate buffer (pH 7.4). Dylight-488 was added to the solution for a final GDNF concentration of 10 mg/mL and a final Dylight-488 concentration of 50 ng/mL and incubated overnight at 4° C. The solution was then dialyzed using Slide-A-Lyzer MINI Dialysis Units (Thermo Scientific, Rockford, Ill., 3500 MWCO) in 8 mM sodium phosphate buffer (pH 7.4) to remove unbound Dylight-488.

Example 16: Confirmation of Gradient Formation

The glass walls of Pasteur pipettes were passivated with PLL(375)-g[7]-PEG(5). The pipettes were filled with a 20 mg/mL PLL-g-PEG solution, incubated for 30 s, and washed with DI water. After sufficient drying time, the tips of the pipettes were sealed with silicone aquarium sealant (DAP Inc., Baltimore, Md.). To form scaffolds, microparticle solutions were sequentially added to the pipettes that were placed in 15 mL conical vials. The microparticle solutions were centrifuged at 1000 g for 5 min before the next layer of microparticles was added (if producing a two-tiered scaffold). The supernatant was then removed once more and replaced with 8 mM sodium phosphate.

Example 17: Confocal Microscopy

Fluorescence microscopy was performed with a Nikon Eclipse C1/80i confocal microscope. Microparticle gradients were imaged while still in the Pasteur pipettes with a 10× objective (NA=0.30, DIC L/N1, WD=16.0 mm). Multiple images were taken along the length of the pipette and processed using EZ-C1 3.70 FreeViewer software (Nikon Instruments Inc.) and then combined. Fluorescence in the composite photographs was analyzed with ImageJ software.

Example 18: Analysis of GDNF Activity Retention $PEG_8$-VS and $PEG_8$-Amine solutions were combined at a 1:1 ratio and diluted to 66.66 mg/mL PEG in PBS. The PEG solution (0.6 mL) was added to each well of a 24 well plate (BD Falcon, Franklin Lakes, N.J.) and incubated at 37° C. for 3 days to ensure maximal crosslinking. Wells were washed 2× with 1 mL PBS before adding 0.6 mL of laminin (0.8 mg/mL) in PBS and incubating at 37° C. overnight. GDNF (833 ng/mL in 8 mM sodium phosphate buffer) was loaded into microparticles as described above. After incubation, microparticles were centrifuged and supernatant was removed. Microparticles were re-suspended in modified neurobasal (MNB) media (Invitrogen, Carlsbad, Calif.) containing 0.1% BSA, 0.5 mM L-glutamine, 2.5 mM L-glutamate, 1% N2 supplement, and 1% antibiotic/antimycotic solution (ABAM) (all from Invitrogen) and quickly centrifuged again to remove free GDNF. Supernatant was removed and the microparticles were re-suspended in MNB media (1 mL of media for about 0.5 mL of loaded microparticles) and incubated 2 h at 4° C. The microparticles were centrifuged once again and the supernatant was transferred to the 24 well plate with PEG gels (1 mL per well). Dorsal root ganglions (DRGs) were dissected from day 10 White Leghorn chicken embryos (Sunrise Farms, Catskill, N.Y.) and placed into wells containing either microparticle MNB media or fresh MNB media (no GDNF). At 24, 48, and 72 h, phase contrast images of the neurite extension from the DRGs were taken with a 4× objective.

Example 19: Conduit Assembly

Figure 6A:
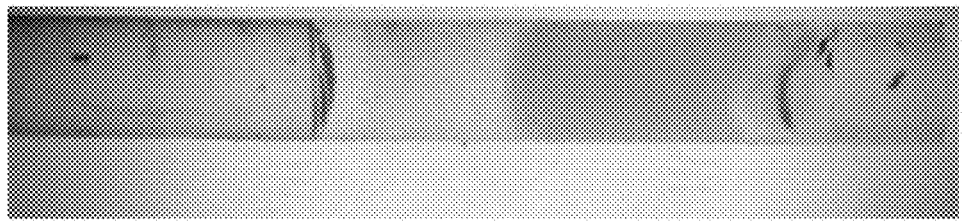
FIG. 6A is a fully formed conduit: microparticle scaffold (blue) flanked by two fibrin plugs, glue plug still intact.
Figure 6B:
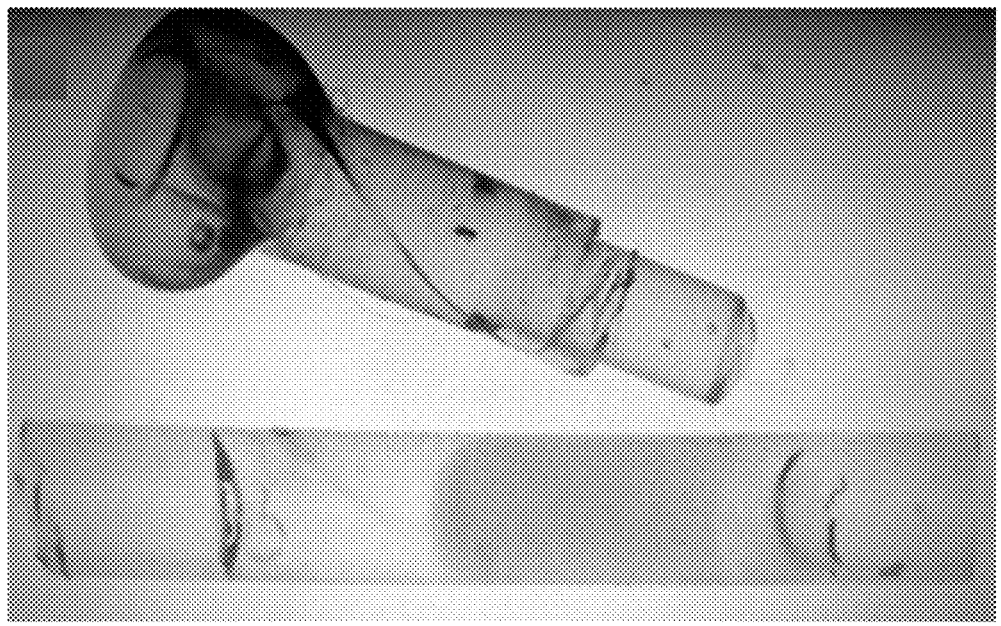
FIG. 6B is a fully formed conduit, glue plug excised that is ready for implantation.

Sections of standard silicone tubing (Helix Medical, Carpinteria, Calif.) (1.47 mm inside diameter×0.39 mm wall thickness) were stretched over the ends of 1 mL pipette tips (Rainin Instrument LLC, Oakland, Calif.) until secure with ~2 cm protruding from the ends. After autoclaving, a small amount of hot glue was drawn into the tube to form a plug (filling about ~3 mm at the bottom of the tube). The plugged conduits were stored under UV light in a sterile cabinet to enhance sterility. Fibrinogen solutions were prepared by dissolving human plasminogen-free fibrinogen in deionized water at 8 mg/mL for 1 h and dialyzing against 4 L of Tris-buffered saline (TBS) (33 mM Tris, 8 g/L NaCl, 0.2 g/L KCl) at pH 7.4 overnight to exchange salts present in the protein solution. The resulting solution was sterilized by filtration through 5.0 and 0.22 mm syringe filters, and the final fibrinogen concentration was determined by measuring absorbance at 280 nm. Components were mixed to obtain the following final solution concentrations: 8 mg/mL fibrinogen, 2.5 mM $Ca^{2+}$, and 1 NIH U/mL of thrombin. Using a 30 gauge syringe (Exel International Medical Products, St. Petersburg, Fla.), this solution was added inside the tube on top of the glue plug such that a 1-2 mm plug of fibrin was formed. The conduits were then incubated for 1 h at 37° C. The pipette tip and conduit were then placed inside a 3-D printed mold designed to allow for centrifugation of the conduit. Microparticles were then added to the pipette tip and centrifuged to form a scaffold within the tube as previously described. The conduit was then cut away from the tip. The supernatant was removed from the microparticles, and another small fibrin plug was added on top of the microparticles. The glue plug was then excised by cutting the silicone tube around the plug 1 mm from the top of the plug and pulling the plug free (FIGS. 6A and B).

Example 20: Experimental Animals

Twenty four adult male Lewis rats (Charles River Laboratories, Wilmington, Mass.), each weighing 250-300 g, were used in this study. All surgical procedures and perioperative care was performed in accordance with the National Institutes of Health guidelines, where NIH guidelines for the care and use of laboratory animals (NIH Publication #85-23 Rev. 1985) have been observed. Animals were randomly assigned to an experimental group in one of two studies. The first study (n=12) assessed the in vivo degradation of the delivery system and preliminary analysis of nerve regeneration using a 13 mm nerve gap injury model. The second study (n=12) quantitatively assessed axonal regeneration into the conduits using a 7 mm nerve gap injury model. This second study also qualitatively assessed the degradation of the delivery system and the presence of a foreign body response, including neutrophil and macrophage accumulation, within the conduits.

Example 21: Operative Procedure

All surgical procedures were performed using aseptic technique and microsurgical dissection and repairs. Under subcutaneous anesthesia with ketamine (75 mg kg$^{-1}$) and medetomidine (0.5 mg kg$^{-1}$), the hind leg of the rat was prepped with betadine and alcohol and the sciatic nerve was exposed through a dorsolateral gluteal muscle splitting incision. An ~5 mm nerve segment was excised proximal to the trifurcation of the sciatic nerve and a nerve guidance conduit was sutured to the transected proximal and distal stumps, incorporating 1 mm of nerve on either end. Two 9-0 nylon interrupted microepineurial sutures were used to secure the conduit at each end, resulting in a tension-free gap between the proximal and distal stumps. Wounds were irrigated with saline, dried and closed with a running 5-0 vicryl suture in muscle fascia, and then interrupted 4-0 nylon skin sutures. Anesthesia in experimental animals was then reversed with a subcutaneous injection of atipamezole HCl (1 mg kg$^{-1}$) (Pfizer Animal Health, Exton, Pa.), and the animals recovered in a warm environment. After recovery, the animals were returned to a central housing facility.

In the first study, at 1, 2, 4, 6, and 8 weeks postoperatively, all animals were re-anesthetized and the conduits/nerves were exposed by reopening the prior muscle splitting incision. At this time, light and fluorescence photomicrographs were taken, and the wounds were re-closed as before. At 8 weeks, the nerve conduit and a 5 mm portion of native nerve both proximally and distally were harvested. The specimens were marked with a proximal suture and stored in 4% paraformaldehyde in PBS (pH 7.4) at 4° C. and then changed to 30% sucrose in PBS at 4° C. until cryosectioning and immunohistochemical analysis was performed. Following the tissue harvest, the animals were then euthanized with intraperitoneal injection of Euthasol (150 mg kg$^{-1}$) (Delmarva Laboratories, Des Moines, Iowa).

In the second study, all animals were re-anesthetized and the conduits/nerves were exposed and harvested at 4 weeks. The nerve conduit and a 5 mm portion of native nerve both proximally and distally were harvested and stored in 3% glutaraldehyde (Polysciences Inc., Warrington, Pa.) in phosphate buffer (pH 7.2). These nerves were assessed for histology and quantification of axonal regeneration using histomorphometry.

Example 22: Immunohistochemistry

Longitudinal sections of the delivery system and regenerated tissue were cut at 10 mm on a cryostat. Slides were stained for S100 with 1:500 rabbit anti-S100 (Dako; GA504) primary antibody followed by goat anti-rabbit Alexa Fluor 555 secondary antibody (ThermoFisher; A-21428), and stained for neurofilament with monoclonal anti-NF-160 primary antibody (Sigma N-5264) followed by goat anti-mouse Alexa Fluor 488 secondary antibody (ThermoFisher; A-11029) using standard immunohistochemistry techniques. Sections were imaged at 20× using the Nanozoomer HT (Hamamatsu, Bridgewater, N.J.) with appropriate optical filters.

Example 23: Histomorphometry

En bloc specimens of the mid-conduit and distal sciatic nerve with the regenerated nerve underwent histomorphometric analysis as previously described. Briefly, nerve was harvested and stored in 3% glutaraldehyde. The nerves were post-fixed in 1% osmium tetroxide and serially dehydrated in ethanol and toluene. The nerves were then embedded in epoxy (Polysciences), and sectioned on an ultramicrotome into 1 mm cross sections. Slides were counter-stained with 1% toluidine blue dye. The slides were then analyzed at 1000× on a Leitz Laborlux S microscope. The Leco IA32 Image Analysis System (Leco, St. Joseph, Mich.) was utilized to quantify nerve fiber counts, fiber width, fiber density, and percent neural tissue. The sections were also analyzed qualitatively for a foreign body response including neutrophil and macrophage presence. All analysis was done by an observer blinded to the experimental groups.

Example 24: GDNF-Containing, Plasmin Degradable, Laminin-Decorated, Clickable Microparticles in Nerve Guidance Conduits Microparticles were incubated for 8, 9, 9.5 or 10 min at 70° C. in the phase separated state during formation to alter their plasmin degradation rates. Note that this elevated temperature is prior to addition of heparin, laminin or growth factor—biological molecules are never exposed to temperatures greater than 37° C. Fully functionalized microparticles containing GDNF were centrifuged into silicone tubes by stretching the silicone tube securely over a 1 mL pipette tip and sealing the other end with hot glue. This was enclosed within a custom made 3D printed mold, which could be inserted into a 15 mL conical vial for centrifugation. The nerve guidance conduit (NGC) was then excised from the pipette tip, and the glue plug was removed (FIG. 6). Fibrin plugs were formed at either end of the scaffold to increase stabilization as the click reaction proceeded (fibrin plugs can be seen in FIGS. 6A and B). Conduits were then ready for in vivo testing.

Figure 6C:
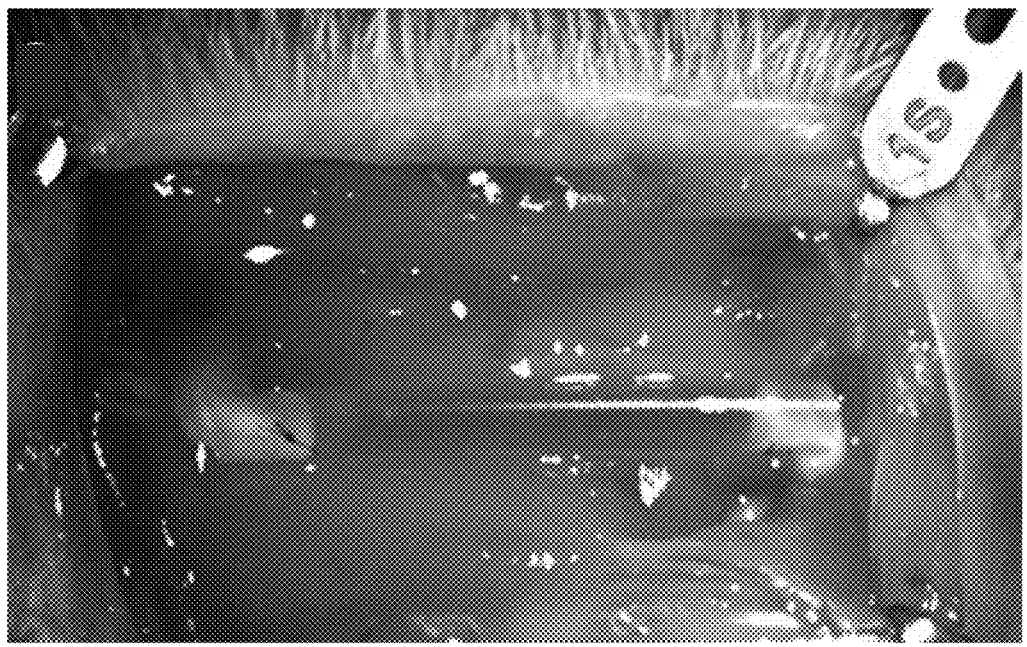
FIG. 6C shows an implanted conduit traversing the severed sciatic nerve in a rat.
Figure 6D:
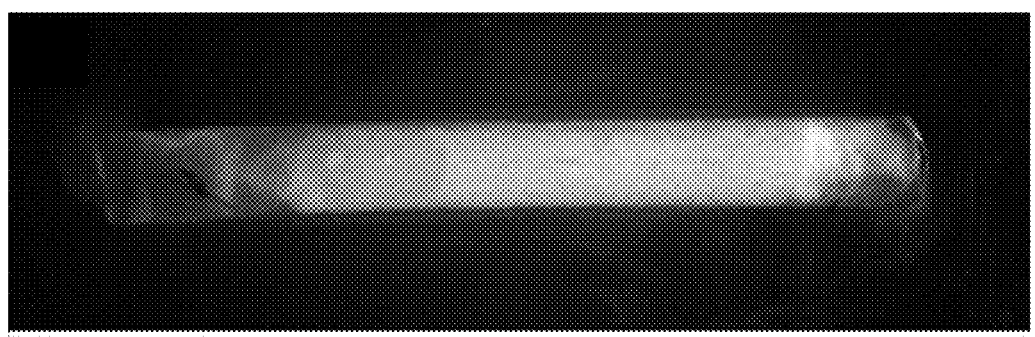
FIG. 6D is a fluorescent photograph of the implanted conduit seen in FIG. 6C.

To assess the in vivo degradation of the delivery system, conduits containing microparticle scaffolds labeled with Dylight-633 were implanted into rats traversing a severed sciatic nerve (FIGS. 6C and D). Scaffolds were about 10 mm in length, with some variation, and with the fibrin plugs the total length of nerve gap was about 13 mm. Fluorescence images indicating the presence of non-degraded scaffold were compared to normal light images of the conduit to determine the percentage of each scaffold's length that had degraded at each time point (Table 1). Table 1 shows the results of in vivo degradation of scaffolds. Conduits containing fluorescently labeled, fully-functionalized PEG microparticle scaffolds with gradients in GDNF were implanted in rats traversing a severed sciatic nerve. Degradation of the scaffolds was evaluated using fluorescence microscopy periodically in living animals. Implants were evaluated visually for the presence of infection or necrosis. The conduits were also evaluated for tissue regeneration across the gap. "Microsphere incubation time" refers to the length of time that microparticles were cross-linked at 70° C. during formation, which was prior to introduction of biologically-derived molecules (heparin, laminin and GDNF). Biological molecules were never exposed to temperatures greater than 37° C.

TABLE 1

| Microsphere Incubation Time | | % Of scaffold degraded | | | | | Observed Infection? | Observed Necrosis? | Observed Tissue? |
| --- | --- | --- | --- | --- | --- | --- | --- | --- | --- |
| | | 7 days in vivo | 14 days in vivo | 32 days in vivo | 41 days in vivo | 55 days in vivo | | | |
| 8 minutes | #1 | 86% | 89% | 96% | 98% | 99% | No | No | No |
| | #2 | 89% | 91% | 96% | 99% | 99% | No | No | No |
| | #3 | 99% | 100% | 100% | 100% | 100% | No | No | Yes |
| 9 minutes | #1 | 0% | 76% | 81% | 83% | 83% | No | No | No |
| | #2 | 0% | 0% | 0% | 2% | 4% | No | No | Yes |
| | #3 | 45% | 57% | 74% | 76% | 84% | No | No | No |
| 9.5 minutes | #1 | 80% | 80% | 98% | 97% | 98% | No | No | No |
| | #2 | 77% | 89% | 91% | 92% | 99% | No | No | No |
| | #3 | 0% | 0% | 0% | 0% | 0% | No | No | Yes |
| 10 minutes | #1 | 0% | 0% | 0% | 0% | 0% | No | No | No |
| | #2 | 0% | 0% | 0% | 0% | 0% | No | No | No |
| | #3 | 0% | 0% | 0% | 0% | 0% | No | No | No |

Figure 7A:
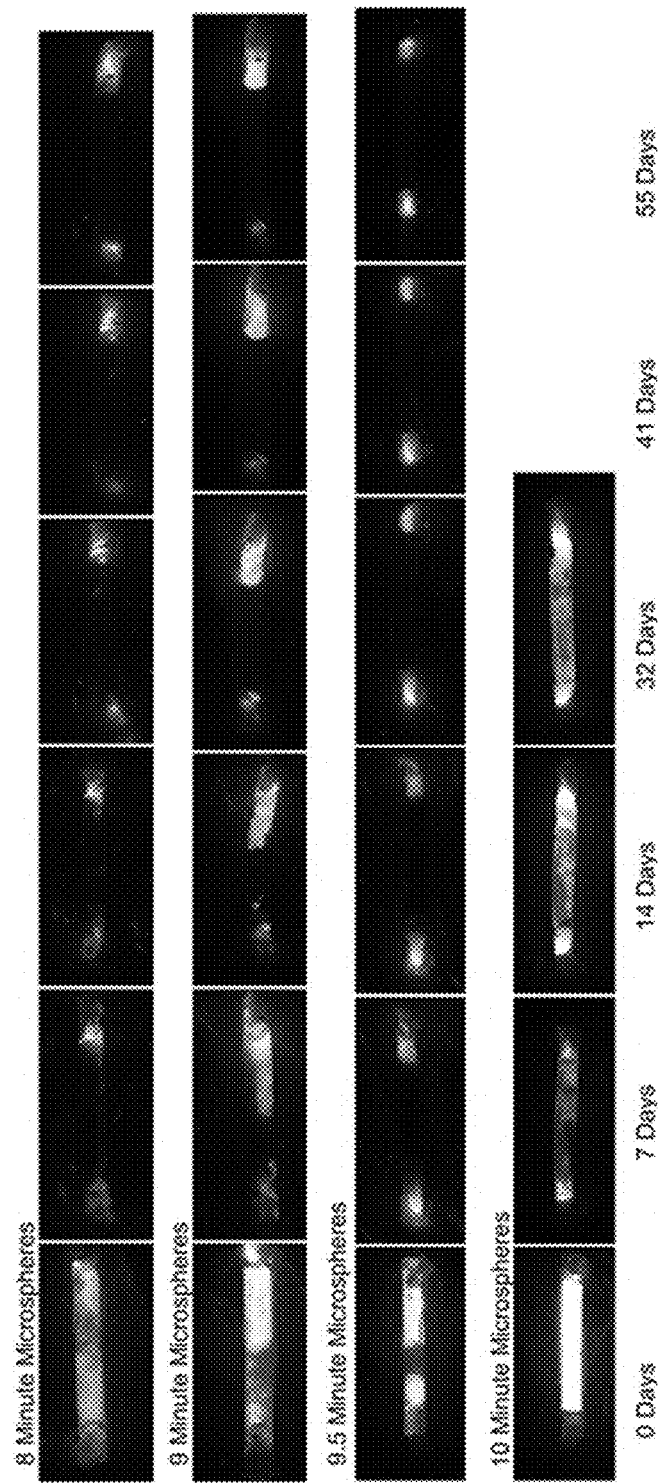
FIG. 7A shows the in vivo degradation of scaffolds. Conduits containing fully-functionalized PEG microparticle scaffolds with gradients in GDNF were implanted in rats traversing a severed sciatic nerve. Degradation of the scaffolds was evaluated using fluorescence microscopy. Sample photographs for each condition are shown.
Figure 7B:
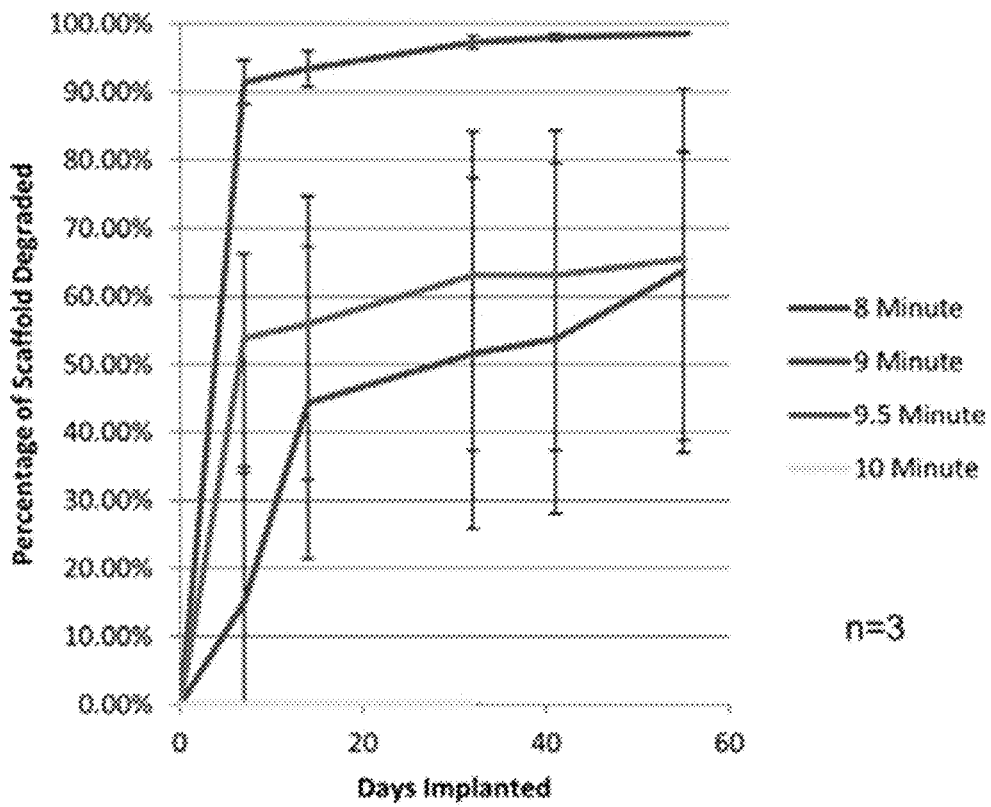
FIG. 7B is a graph showing average percentage of the scaffold degraded over time for each condition.
Figure 8:
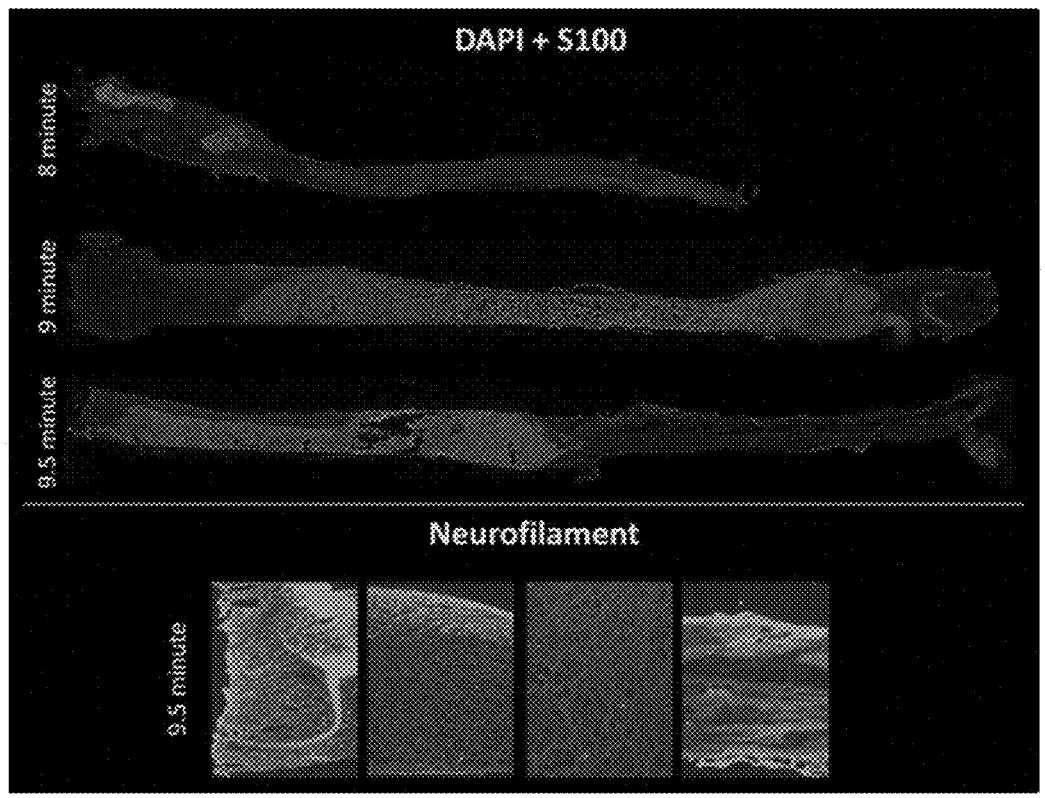
FIG. 8 shows IHC for regenerated tissue. Fluorescent photomicrographs of sectioned tissue harvested from NGC's at 8 weeks. S100 (red; Schwann cell marker) layered with DAPI (blue) staining over the whole length of the tissue is shown for the 3 instances of regeneration (occurring in different microparticle incubation time conditions). Sample fluorescent photomicrographs at higher magnification (100x) of tissue stained for neurofilaments (green) shown for the 9.5 min condition.
Figure 9A:
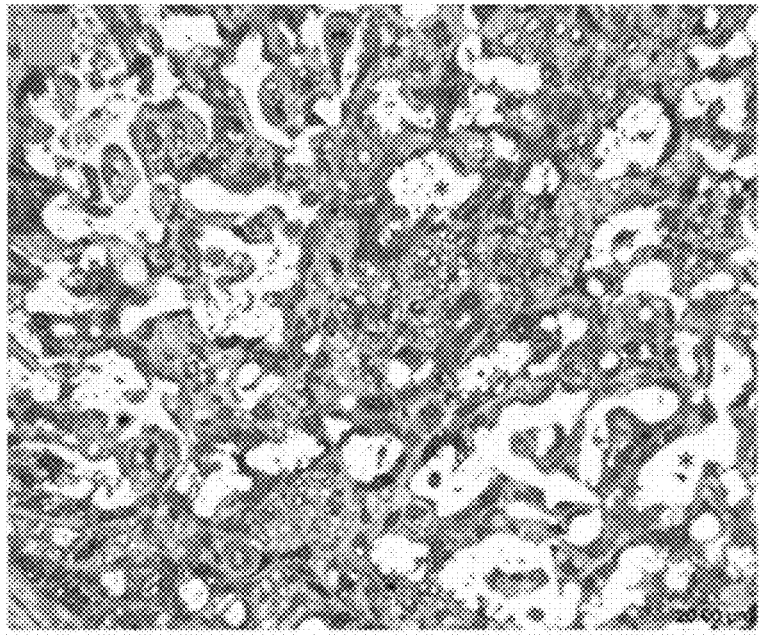
FIG. 9A is a representative photomicrograph of axonal regeneration within the scaffolds, taken at the mid-conduit level. Note the presence of nerve regeneration evidenced by the presence of myelinated axons (clear circular area surrounded by dark ring) as well as scaffold degradation (red asterisks).
Figure 9B:
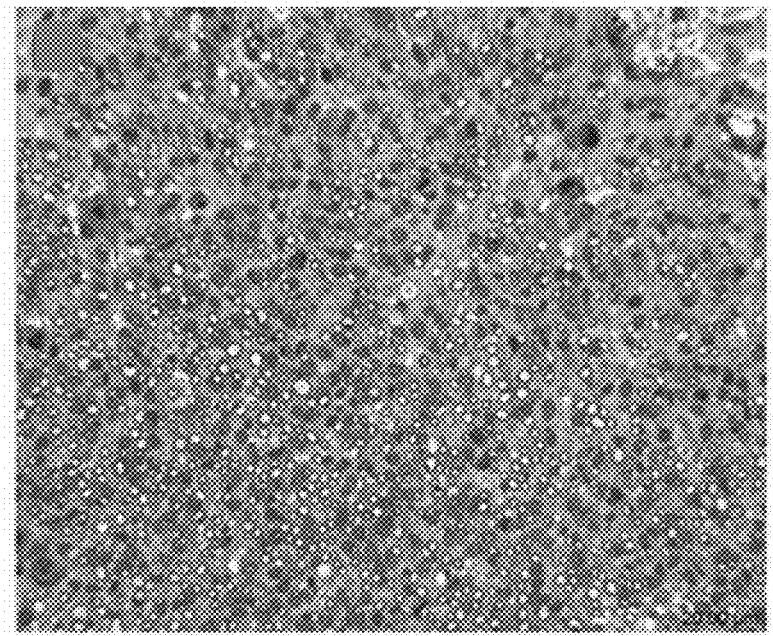
FIG. 9B is a photomicrograph (mid-conduit level) of scaffold with the most extensive nerve regeneration, with most of the scaffold degraded and the highest number of axons.
Figure 9C:
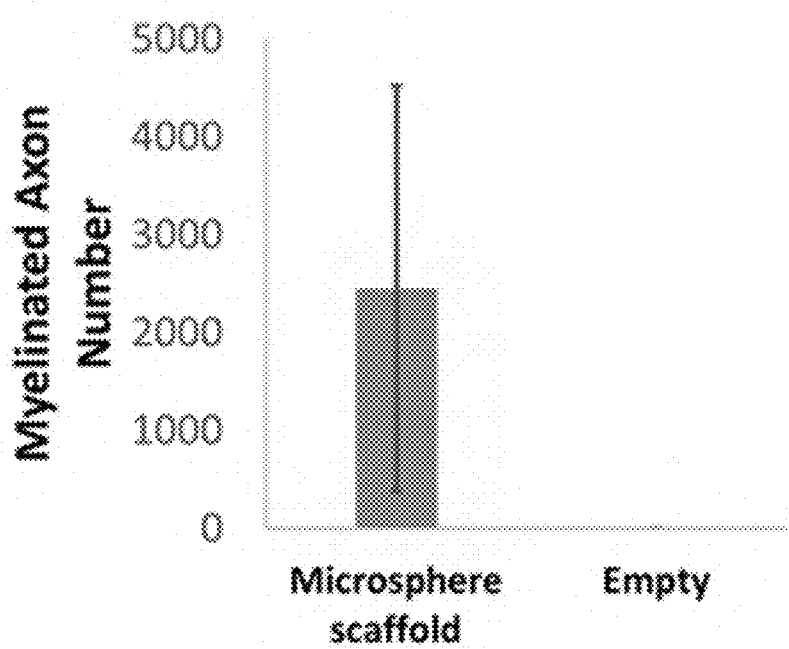
FIG. 9C shows scaffolds promoted robust axonal regeneration at the mid-conduit level while an empty conduit did not promote any axonal regeneration. Average with standard error of the mean is shown.
Figure 9D:
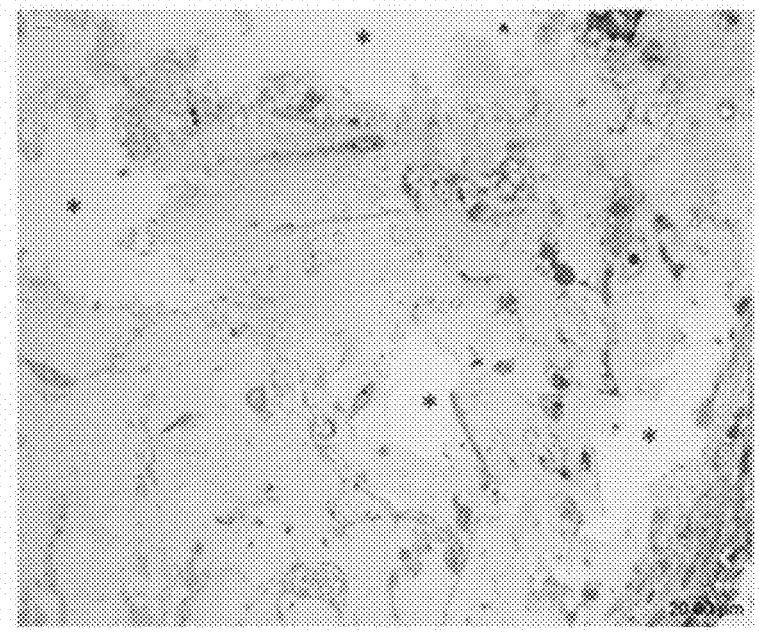
FIG. 9D shows the distal portion of the conduit demonstrated more scaffold degradation and less tissue regeneration.

Example fluorescence photographs and a graphical representation of the typical amounts of degradation can be seen in FIG. 7. Most scaffolds composed of microparticles were largely degraded after 1 week, except those that were incubated in the phase separated state at 70° C. for 10 min during microparticle formation. In the conduits that did incur an appreciable amount of degradation over their length, some differences were observed in their rates of degradation. The conduits formed from '8 min' microparticles, especially, degraded faster than the scaffolds with longer incubation times. There was no appreciable change in the length of the scaffolds composed of microparticles incubated at 70° C. for 10 min, although very small patches of degradation were observed, suggesting that the scaffolds were degradable. Patchy degradation was also observed for one out of three conduits with microparticles incubated for 9 min and 9.5 min. However, unexpectedly, substantial tissue regeneration resulted across the nerve gap. Immunohistochemistry for the three cases of regenerated tissue is shown in FIG. 8. In the 9 and 9.5 min cases, a porous structure can be seen where the scaffold did not degrade (as determined by the presence of fluorescence of Dylight-633). DAPI staining revealed cell growth throughout the tissue in all cases, while S100 staining indicated the presence of Schwann cells in the scaffold-containing regions. Staining for neurofilaments (NF-160) was weak and did not indicate the presence of axons. All conduits were also evaluated for any observed infection or necrosis (Table 1). None of the conduits were observed to elicit either of these negative biological reactions. To quantitatively assess axonal regeneration into the conduits and scaffolds, as well as the presence of a foreign body response, conduits containing fully functionalized '9 min' microparticles were implanted into the rat sciatic nerve injury gap model. FIGS. 9A-9D show axonal regeneration within scaffolds. Conduits containing fully-functionalized PEG microparticle scaffolds without growth factor were implanted in rats traversing a severed sciatic nerve and compared to empty conduits. In this instance, the PEG scaffold was 5 mm in length with the fibrin plugs again at the ends to yield a total gap of ~7 mm, which was compared to an empty conduit of a similar gap. None of the conduits contained GDNF, so as to focus on material effects rather than growth factor effects. After 4 weeks, conduits were assessed by histomorphometry at the mid-conduit level to determine if the scaffold promoted nerve regeneration. Conduits containing scaffolds promoted robust nerve regeneration including axonal regeneration in most animals (5 of 6 had regenerated axons mid-conduit) (FIG. 9B). Conduits without the scaffold (empty) did not regenerate any axons (0 of 6 had regenerated axons mid-conduit). In addition, conduits containing the scaffolds did not qualitatively demonstrate the presence of a foreign body response, including neutrophil or macrophage accumulation or a fibrotic response, as assessed by histomorphometry. Further distal to the mid-conduit level, the scaffolds demonstrated increased degradation as noted by larger scaffold voids which corresponded with less cellular migration and repopulation of these areas (FIG. 9D). Well vascularized connective tissue was observed adjacent to the silicone conduit but not within the scaffold.

Example 25: Use of Suspension Polymerization to Form Microparticles $PEG_8$-VS solution (200 mg/mL in PBS) is combined with plasmin degradable $PEG_8$-VS (PEG-(VRN)$_8$) solutions (200 mg/mL in PBS) at a 1:1 molar ratio and incubated at 37° C. in a solution of 20% dextran with rapid stirring overnight. The formed enzyme-sensitive microparticles are collected by centrifugation and washed 3× with PBS. The microparticles are separated into two batches and reacted either with cyclooctyne-(VRN)-(VRN)-PEG-amine or azide-(VRN)-(VRN)-PEG-amine. The inclusion of two VRN enhances plasmin degradability compared to a single VRN per PEG chain. The two types of microspheres are centrifuged into a silicone tube and allowed to react overnight to form a nerve guidance conduit.

Having described several embodiments, it will be recognized by those skilled in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Those skilled in the art will appreciate that the presently disclosed embodiments teach by way of example and not by limitation. Therefore, the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A modular scaffold comprising a plurality of hydrogel microparticles, wherein the hydrogel microparticles are crosslinked together with at least some crosslinks having tunable rates of enzymatic degradation, wherein the crosslinks is the plasmin sensitive peptide sequence Ac-GCG-GVRNGGK-NH2.

2. The modular scaffold of claim 1, wherein the scaffold comprises a gradient of degradation between the microparticles.

3. The modular scaffold of claim 2, wherein microparticles with at least two different rates of degradability are layered to form the gradient of degradation in the scaffold.

4. The modular scaffold of claim 3, wherein the gradient of degradation has a length scale greater than the mean size of the microparticles.

5. The modular scaffold of claim 1, wherein the crosslinks between the microparticles fully degrade before the bulk of the microparticles fully degrades.

6. The modular scaffold of claim 1, wherein the microparticles comprise a cross-linked water-soluble polymer.

7. The modular scaffold of claim 6, wherein the water-soluble polymer is selected from the group consisting of polyacrylate, polyacrylamide, poly(acrylamide sulphonic acid), polyacrylonitrile, polyamines, poly(ethylene glycol), poly(ethylene imine), poly(ethylene oxide), poly(ethyloxazoline), polyhydroxyethylacrylate, polymethacrylate, polymethacrylamide, poly(oxyalkylene oxide), poly(propylene oxide), polyurethane, poly(vinyl alcohol), poly(vinyl pyrrolidone), and combinations thereof.

8. The modular scaffold of claim 1, wherein at least a portion of the crosslinks between the microparticles are formed using Click chemistry.

9. The modular scaffold of claim 1, wherein the microparticles further comprise a functional agent.

10. The modular scaffold of claim 9, wherein the functional agent is selected from the group consisting of cell adhesion proteins, growth factors, extra cellular matrix components, and combinations thereof.

11. The modular scaffold of claim 10, wherein the cell adhesion protein is laminin.

12. The modular scaffold of claim 11, wherein the growth factor is glial cell-derived neurotrophic factor (GDNF).

13. The modular scaffold of claim 12, wherein the microparticles further comprise heparin.

14. The modular scaffold of claim 13, wherein the heparin content of the microparticles is greater than about 3% by weight.

15. The modular scaffold of claim 9, wherein the scaffold comprises a concentration gradient of the functional agent.

16. The modular scaffold of claim 1, wherein the scaffold is contained within a nerve guidance conduit.

17. The modular scaffold of claim 1, wherein the scaffold is seeded with or encourages the in-growth of cells selected from the group consisting of fibroblasts, epithelial cells, blood cells, precursor blood cells, immune system cells, hepatocytes, renal cells, chondrocytes, osteoblasts, respiratory tract cells, gut cells, bladder cells, pancreatic cells, myoblasts, skeletal muscle cells, heart muscle cells, smooth muscle cells, exocrine gland cells, hormone secreting cells, sensory transducer cells, neurons, neuron supporting cells, stem cells, and combinations thereof.

18. The modular scaffold of claim 17, wherein the cells are neurons, neuron supporting cells, or combinations thereof.

* * * * *